US006638764B2

(12) United States Patent
Schreiber et al.

(10) Patent No.: US 6,638,764 B2
(45) Date of Patent: Oct. 28, 2003

(54) METHODS OF INHIBITING PHAGOCYTOSIS

(75) Inventors: Alan D. Schreiber, Philadelphia, PA (US); Jong-Gu Park, Drexel Hill, PA (US)

(73) Assignee: University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/811,492

(22) Filed: Mar. 20, 2001

(65) Prior Publication Data

US 2002/0068703 A1 Jun. 6, 2002

Related U.S. Application Data

(63) Continuation of application No. 09/158,980, filed on Sep. 14, 1998, now Pat. No. 6,242,427, which is a continuation of application No. 08/657,884, filed on Jun. 7, 1996, now Pat. No. 5,858,981, which is a continuation-in-part of application No. 08/483,530, filed on Jun. 7, 1995, now abandoned, which is a continuation-in-part of application No. 08/316,425, filed on Sep. 30, 1994, now abandoned, which is a continuation-in-part of application No. 08/129,381, filed on Sep. 30, 1993, now abandoned.

(51) Int. Cl.$^7$ .......................... C12Q 1/68; G01N 33/53; C12P 21/06; A01N 37/18; C07H 21/04
(52) U.S. Cl. ................... 435/375; 435/60; 435/455; 435/69.1; 514/2; 514/16; 514/44; 536/24.5
(58) Field of Search ............................. 514/2, 44, 16; 435/6, 7.1, 375, 69.1, 455; 536/24.5

(56) References Cited

U.S. PATENT DOCUMENTS

| 4,686,282 A | 8/1987 | Hahn |
| 5,189,014 A | 2/1993 | Cowan, Jr. |

FOREIGN PATENT DOCUMENTS

| EP | 0 614 978 | 9/1994 |
| WO | WO 91/06570 | 5/1991 |
| WO | WO 93/21317 | 10/1993 |
| WO | WO 95/09002 | 4/1995 |

OTHER PUBLICATIONS

Indik et al., Blood, 1994, 83, 2072–2080.*
Van den Herik–Oudijk. et al., J of Immunol, 152:574. 1994.*
Daeron et al. International Immunology, 1993, 5, 1393–1401.*
Mountain TIBTECH 2000, 18:119–128.*
Letourneur et al, "Characterization of the Family of Dimers Associated with Fc Receptors (FcεRI FcγRIII)", The Journal of Immunology 147(8):2652–2656 (1991).
Takai et al, FcRγ Chain Deletion Results in Pleiotrophic Effector Cell Defects, Cell 76:519–529 (1994).
Turner et al, "Perinatal lethality and blocked B–cell development in mice lacking the tyrosine kinase Syk", Nature 378:298–306 (1995).

Porteous et al, "Evidence for safety and efficacy of DOTAP cationic liposome mediated CFTR gene transfer to the nasal epithelium of patients with cystic fibrosis", Gene Therapy 4:210–218 (1997).
Bonn, "Prospects for antisense therapy are looking brighter", Science and Medicine 347:820–821 (1996).
Stein et al, "Antisense Oligonucleotides as Therapeutic Agents—Is the Bullet Really Magical", Science 261:1004–1012 (1993).
Roush, "Antisense Aims for a Renaissance", Science 276:1192–1193 (1997).
Alton et al, "Non–invasive liposome–meidated gene delivery can correct the ion transport defect in cystic fibrosis mutant mice", Nature Genetics 5:135–142 (1993).
Chan et al, "Differential Expression of ZAP–70 and Syk Protein Tyrosine Kinases, and the Role of This Family of Protein Tyrosine Kinases in TCR Signaling", Journal of Immunology, pp. 4758–4766 (1994).
Zelphati t al, "Intracellular Distribution and Mechanism of Delivery of Oligonucleotides Mediated by Cationic Lipids", Pharmaceutical Research 13(9):1367–1372 (1996).
Stull et al, "Antigene, Ribozyme and Aptamer Nucleic Acid Drugs: Progress and Prospects", Pharmaceutical Research 12(4):465–483 (1995).
Maekawa et al, "Induction of Fc epsilon RII/CD23 on PHA–activated human peripheral blood T lymphocytes and association of fyn tyrosine kinase with Fc epsilon RII/CD23", Int. J. Tissue React. 14(3):121–130 (1992)—Abstract.
Sugie et al, "Fyn tyrosine kinase associated with Fc epsilon RII/CD23: possible multiple roles in lymphocyte activation", Proc. Natl. Acad. Sci. USA 88(20):9132–9135 (1991)—Abstract.
Richards et al, "Biology and chemistry of low affinity IgE receptor (Fc epsilon RII/CD23)", Crit. Rev. Immunol. 11(2):65–86 (1991)—Abstract.
Yodoi et al, "Low affinity IgE receptors: regulation and functional roles in cell activation", Ciba Found. Symp. 147:133–148 (1989)—Abstract.
Mehta et al, "Eosinophil as a therapeutic target in allergic disease", Compr. Ther. 20(11):651–657 (1994)—Abstract.

(List continued on next page.)

Primary Examiner—Christina Chan
Assistant Examiner—Michail A Belyavskyi
(74) Attorney, Agent, or Firm—Nixon & Vanderhye P.C.

(57) ABSTRACT

The present invention relates, in general, to methods of treating diseases resulting from interactions between immune complexes and Fc receptors. In particular, the present invention relates to methods of modulating the clearance of antibody-coated cells from the circulation by inhibiting phagocytosis and to methods of modulating the interaction of immune complexes with tissue Fc receptors. Further, the invention relates to methods of modulating the activation of immunological processes mediated by Fc receptor activation resulting from antibody-antigen/receptor interaction.

4 Claims, 15 Drawing Sheets

OTHER PUBLICATIONS

Kiehntopf et al, "Ribozyme–mediated cleavage of the MDR–1 transcript restores chemosensitivity in previously resistant cancer cells", The EMBO Journal 13(19):4645–4652 (1994).

Akhtar et al, "Interactions of antisense DNA oligonucleotide analogs with phospholipid membranes (liposomes)", Nucleic Acids Research 19(20):5551–5559 (1991).

Thierry et al, "Overcoming Multidrug Resistance in Human Tumor Cells Using Free and Liposomally Encapsulated Antisense Oligonucleotides", Biochemical and Biophysical Research Communication 190(3):952–960 (1993).

Zelphati et al, "Antisense oligonucleotides in solution or encapsulated in immunoliposomes inhibit replication of HIV–1 by several different mechanisms", Nucleic Acids Researchs 22(20):4307–4317 (1994).

Aoki et al, "Liposome–mediated in Vivo Gene Transfer of Antisense K–ras Construct Inhibits Pancreatic Tumor Dissemination in the Murine Peritoneal Cavity", Cancer Research 55:3810–3816 (1995).

Lewis et al, "A serum–resistant cytofectin for cellular delivery of antisense oligodeoxynucleotides and plasmid DNA", Proc. Natl. Acad. Sci USA 93:3176–3181 (1996).

Sugimoto et al, "Oligomannose–coated liposomes as an adjuvant for the induction of cell–mediated immunity", FEBS Letters 363:53–56 (1995).

Grimaldi et al, "Attempts to use liposomes and RBC ghosts as vectors in drug and antisense therapy of virus infection", Res. Virol. 148:177–180 (1997).

Wang et al, "Delivery of antisense oligodeoxyribonucleotides against the human epidermal growth factor receptor into cultured KB cells with liposomes conjugated to folate via polyethylene glycol", Proc. Natl. Acad. Sci. USA 92:3318–3322 (1995).

Koff et al, "Protection of Mice Against Fatal Herpes Simplex Type 2 Infection by Liposomes Containing Muramyl Tripeptides", Science, pp. 495–497 (Apr. 26, 1985).

Ohishi et al, "Peptide–Based Bovine Leukemia Virus (BLV) Vaccine That Induces BLV–Env Specific Th–1 Type Immunity", Leukemia 11: Suppl. 223–226 (1997).

Francis et al, "Efficacy of Unilamellar Liposomal Amphotericin B in Treatment of Pulmonary Aspergillosis in Persistently Granulocytopenic Rabbits: The Potential Role of Bronchoalveolar D–Mannitol and Serum Galactomannan as Markers of Infection", The Journal of Infectious Diseases 169:356–368 (1994).

Demoly et al, "IgE produces monocyte superoxide anion release" Correlation with CD23 expression, J. Allergy Clin. Immunol. 93(1)/Part 1:108–116 (1994).

Vignola et al, "Phenotypic and Functional Modulation of Normal Human Alveolar Macrophages by Histamine", Am. J. Respir. Cell Mol. Biol. 11:456–463 (1994).

Inagaki, "An Increase in Superoxide Generation of Bronchoalveolar Lavage Fluids in the Model of Late Asthmatic Response in Guinea Pigs", Journal of Asthma 30(5):401–405 (1993).

Jarjour et al, "Enhanced production of oxygen radicals in asthma", J. Lab. Clin. Med. 123:131–136 (1994).

Vachier et al, "Imaging Reactive Oxygen Species in Asthma", J. Biolumin. Chemilumin. 9:171–175 (1994).

Curtis et al, "New Concepts in the Pathogenesis of Immune Lung Injury", Seminars in Respiratory Medicine 12(3):156–174 (1991).

Hallsworth et al, "Selective enhancement of GM–CSF, TNF–$\alpha$, IL–1$\beta$ and IL–8 production by monocytes and macrophages of asthmatic subjects", Eur. Respir. J. 7:1096–1102 (1994).

Callerame et al, "Immunologic Reactions of Bronchial Tissues in Asthma", The New England Journal of Medicine 284(9):459–463 (1971).

Wasserman, "Mast Cells and Airway Inflammation in Asthma", Am. J. Respir. Cri. Care Med. 150:539–541 (1994).

Bitterman et al, "Alveolar Macrophage Replication One Mechanism for the Expansion of the Mononuclear Phagocyte Population in the Chronically Inflamed Lung", The Journal of Clinical Investigations, Inc. 74:460–469 (1984).

Chanez et al, "Modulation by interleukin–4 of cytokine release from mononuclear phagocytes in asthma", J. Allergy Clin. Immunol. 94(6)/Part 1:997–1005 (1994).

Johnson et al, "Role of Oxygen Metabolites in Immune Complex Injury of Lung", The Journal of Immunology 126(6):2365–2369 (1981).

Warner et al, "Lung Sources and Cytoline Requirements for In Vivo Expression of Inducible Nitric Oxide Synthase", J. Respir. Cell Mol. Biol. 12:649–661 (1995).

Demoly et al, "IFN–$\gamma$ activates superoxide anion production in blood monocytes from allergic asthmatic patients", Annals of Allergy, Asthma, & Immunology 75:162–166 (1995).

Curran, "The Role of Nitric Oxide in the Development of Asthma", Int. Arch. Allergy Immunol. 111:1–4 (1996).

Kay et al, "Eosinophils and Eosinophil–Associated Cytokines in Allergic Inflammation", Int. Arch. Allergy Immunol. 113:196–199 (1997).

Venge et al, "Eosinophil Activation in Allergic Disease", Int. Archs. Allergy appl. Immun. 82:333–337 (1987).

Weller, "Roles of eosinophils in allergy", Current Opinion in Immunology 4:782–787 (1992).

Bittleman et al, "Allergic models and cytokines", Am. J. Respir. Crit. Care Med. 150(5 Pt. 2):S72–S76 (1994).

Barnes, "Cytokines as Mediators of Chronic Asthma", Am. J. Respir. Crit. Care Med. 150:S42–S49 (1994).

Bousquet et al, "Eosinophil Inflammation in Asthma", Am. J. Respir. Crit. Care Med. 150:S33–S38 (1994).

Kunkel et al, "Macrophage–Derived Cytokines in Lung Inflammation", pp. 183–201.

Ra et al, "A Macrophage Fc$\gamma$ receptor and the mast cell receptor for IgE share an identical subunit", Nature 341:752–754 (1989).

Darby et al, "Stimulation of Macrophage Fc$\gamma$RIIIA Activates the Receptor–Associated Protein Tyrosine Kinase Syk and Induces Phosphorylation of Multiple Proteins Including p95Vav and p62/GAP–Associated Protein", Journal of Immunology 152:5429–5437 (1994).

Indik et al, "Induction of Phagocytosis by a Protein Tyrosine Kinase", Blood 85(5):1175–1180 (1995).

Park et al, "Determinants of the phagocytic signal mediated by the type IIIA Fc$\gamma$ receptor, Fc$\gamma$RIIIA: Sequence requirements and interaction with protein–tyrosine kinases", Proc. Natl. Acad. Sci. USA 92:7381–7385 (1995).

Matsuda et al, "Abrogation of the Fc$\gamma$ Receptor IIA–mediated Phagocytic Signal by Stem–Loop Syk Antisense Oligonucleotides", Molecular Biology of the Cell 7:1095–1106 (1996).

Ramaswamy et al, "Pulmonary immune responses to *Nippostrongylus brasiliensis*: isotype–specific antibodies in bronchoalveolar lavage fluids of rats", Parasite Immunology 15:573–582 (1993).

Viksman et al, "Phenotypic Analysis of Alveolar Macrophages and Monocytes in Allergic Airway Inflammation", Am. J. Respir. Crit. Care Med. 155:858–863 (1997).

Vachier et al, "Increased Oxygen Species Generation in Blood Monocytes of Asthmatic Patients[1–3]", Am. Rev. Respir. Dis. 1161–1166 (1992).

Nyce et al, "DNA antisense therapy for asthma in an animal model", Nature 385:721–725 (1997).

Wagner, Gene inhibition using antisense oligodeoxynucleotides, Nature 372:333–335 (1994).

Gura, Antisense Has Growing Pains, Science 270:575–577 (1995).

Clynes et al, "Cytotoxic Antibodies Trigger Inflammation Through Fc Receptors", Immunity 3:21–26 (1995).

Park et al, "In the Absence of Other Fc Receptors, FcγRIIIA Transmits a Phagocytic Signal That Requires the Cytoplasmic Domain of Its γ Subunit", J. Clin. Invest. 92:1967–1973 (1993).

Clark et al, "Analysis of Ig–α–tyrosine kinase interactions reveals two levels of binding specificity and tyrosine phosphorylated Ig–α stimulation of Fyn activity", The EMBO Journal 13(8):1911–1919 (1994).

Ohishi et al, "Peptide–Based Bovine Leukemia Virus (BLV) Vaccine That Induces BLV–Env Specific Th–1 Type Immunity", Leukemia 11:Suppl 223–226 (1997).

Kunkel et al, "Macrophage–Derived Cytokines in Lung Inflammation", In: Lung and Dendritic Cells in Health and Disease (Mary F. Lipscomb and Stephen W. Russell, eds.) Marcel Dekker, Inc., New York, pp. 183–202 (1997).

Stull and Szoka, Pharmaceutical Research 12:465–483 (1995).

Rousch, Science 276:1192–1193 (1997).

Hunter et al, "Activation of the Fcγ Receptor FcγRIIB Negatively Regulates Phagocytosis by the Fcγ Receptor FcγRIIA", FASEB Journal 10(6):2084 (1996)—Abstract.

Hunter et al, "Inhibition of Fcγ Receptor–Mediated Phagocytosis by a Nonphagocytic Fcγ Receptor", Blood 91(5):1762–1768 (1998).

Keegan and Paul, "Multichain immune recognition receptors: similarities in structure and signaling pathways", Immunology Today 13(2):63–68 (1992).

Sautes et al, Soluble FcγR (sFcγR): Detection in Biological Fluids and Production of a Murine Recombination sFcγR Biologically Active in vitro and in vivo, Immunobiol. 185:207–221 (1992).

Agrawal, TIBTech 14:376–387 (1996).

Branch, TIBS 23:45–50 (1998).

Law et al, "Molecular Cloning of Human Syk", The Journal of Biological Chemistry 269(16):12310–12319 (1994).

Matsuda et al, "Abrogation of the Fcγ Receptor IIA–mediated Phagocytic Signal by Stem–Loop Syk Antisense Oligonucleotides", Molecular Biology of the Cell 7:1095–1106 (1996).

\* cited by examiner

FIG. 3

Stem | Loop

Human γ chain and rat β-actin primer were used as a control.

(A)

(B)

(C)

Effect of syk antisense ODNS on mRNA levels in RBL-2H3 cells. (A) Syk mRNA, (B) β-actin mRNA, (C) γ chain mRNA.

Lane 1: antisense, Lane 2: sense, Lane 3: Dotap, Lane 4: No DNA,Dotap.

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

GCAGATGCTG TCTACACGGG CCTGAACACC CGGAGCCAGG AGACATATGA GACTCTGAAG      60

(2) INFORMATION FOR SEQ ID NO: 2:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 2:

Ala Asp Ala Val Tyr Thr Gly Leu Asn Thr Arg Ser Gln Glu Thr Ty
1             5                    10                 15

Glu Thr Leu Lys
         20

(2) INFORMATION FOR SEQ ID NO: 3:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

GCAGATGCTG TCTTCACGGG CCTGAACACC CGGAGCCAGG AGACATATGA GACTCTGAAG    60

(2) INFORMATION FOR SEQ ID NO: 4:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GCAGATGCTG TCTACACGGG CCTGAACACC CGGAGCCAGG AGACATTTGA GACTCTGAAG    60

(2) INFORMATION FOR SEQ ID NO: 5:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GCAGATGCTG TCTTCACGGG CCTGAACACC CGGAGCCAGG AGACATTTGA GACTCTGAAG    60

(2) INFORMATION FOR SEQ ID NO: 6:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO: 6:

Glu Xaa Xaa Xaa Xaa Xaa Xaa Xaa Xaa Asp Xaa Xaa Tyr Xaa Xaa
1               5                   10                  15

Leu Xaa Xaa Xaa Xaa Xaa Xaa Xaa Xaa Xaa Xaa Xaa Tyr Xaa Xa
            20                  25                  30

(2) INFORMATION FOR SEQ ID NO: 7:

(i) SEQUENCE CHARACTERISTICS:
        (A) LENGTH: 10 amino acids
        (B) TYPE: amino acid
    (D) TOPOLOGY: linear (ii) MOLECULE TYPE: protein (ix) FEATURE:
        (A) NAME/KEY: Modified-site
        (B) LOCATION: 1
        (D) OTHER INFORMATION: /label= Xaa
            /note= "first and third Xaa is D/E; second Xaa is
            (Xaa)2,7; fourth and sixth Xaa is (Xaa)2; and fifth Xaa is (Xaa)7"

(xi) SEQUENCE DESCRIPTION: SEQ ID NO: 7:

Xaa Xaa Tyr Xaa Leu Xaa Tyr Xaa Leu
1               5                   10

(2) INFORMATION FOR SEQ ID NO: 8:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 8:

Tyr Xaa Xaa Leu
1

(2) INFORMATION FOR SEQ ID NO: 9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CGCTGTCAGC CATGCCG                                            17

(2) INFORMATION FOR SEQ ID NO: 10:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GGGGGGGCTG TCAGCCATGC CGTGTCTTGT CTTTGTCGCT TCTTGAGGAG CCCCCCC    57

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GCCCAAGATG ATTCCAG                                            17

(2) INFORMATION FOR SEQ ID NO: 12:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

```
ATGGAATCAT CTTGGGCATT CATTCGTTCC TCAAAGAAGA ATATGAA                    47
```

(2) INFORMATION FOR SEQ ID NO: 13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
GGTGTGTGCC CTCCGGCC                                                    18
```

(2) INFORMATION FOR SEQ ID NO: 14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
CTGCAGGTTC CATGT                                                       15
```

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
GGGAGTGGTA GTGGCAGAGG                                                  20
```

(2) INFORMATION FOR SEQ ID NO: 16:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

```
ATTGCCCGCC ATGTCT                                                      16
```

(2) INFORMATION FOR SEQ ID NO: 17:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
GATTTGATTC TTGAG                                                       15
```

(2) INFORMATION FOR SEQ ID NO: 18:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

ATTTGGTAGT ATCCCT                                                                    16

(2) INFORMATION FOR SEQ ID NO: 19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

TTTGGCAACA TCACCCGG                                                             18

(2) INFORMATION FOR SEQ ID NO: 20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

ACTTATGATG GCTTGCTC                                                          18

(2) INFORMATION FOR SEQ ID NO: 21:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

TGCCTGCTGC ACGAAGGGAA GGTGCTGCAC TATCGCATCG ACAAAGACAA GACAGGGAA        59

(2) INFORMATION FOR SEQ ID NO: 22:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

GGAAGGTGCT GCACTATCGC ATCGACAAAG ACAAGACAGG GAAGCTCTCC ATCC             54

(2) INFORMATION FOR SEQ ID NO: 23:

(i) SEQUENCE CHARACTERISTICS:
        (A) LENGTH: 53 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 23:

GCAGCGACAA AGACAAGACA GGGAAGCTCT CCATCCCCGA GGGAATATAA AGC         53

(2) INFORMATION FOR SEQ ID NO: 24:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 24:

GGGGGGGCTG TCAGCCATGC CGTGTCTTGT CTTTGTCGCT TCTTGAGGAG CCCCCCC      57

(2) INFORMATION FOR SEQ ID NO: 25:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 25:

CTGTCAGCCA TGCCG                                                    15

(2) INFORMATION FOR SEQ ID NO: 26:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 26:

GCTTCTTGAG GAG                                                      13

(2) INFORMATION FOR SEQ ID NO: 27:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 27:

TGTCTTGTCT TTGTC                                                    15

(2) INFORMATION FOR SEQ ID NO: 28:

(i) SEQUENCE CHARACTERISTICS:
            (A) LENGTH: 60 base pairs
            (B) TYPE: nucleic acid
            (C) STRANDEDNESS: single
            (D) TOPOLOGY: linear

```
            (ii) MOLECULE TYPE: DNA (genomic)

(xi) SEQUENCE DESCRIPTION: SEQ ID NO: 28:

GCCGCGGTTG CCCGCCATGT CTGATTTGAT TCTTGAGATT TGGTAGTATC CCTCCGCGGC      60

(2) INFORMATION FOR SEQ ID NO: 29:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 29:

CTGTCAGCCA TGCCG                                                      15

(2) INFORMATION FOR SEQ ID NO: 30:

(i) SEQUENCE CHARACTERISTICS:
                (A) LENGTH: 13 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 30:

GCTTCTTGAG GAG                                                        13

(2) INFORMATION FOR SEQ ID NO: 31:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 31:

TGTCTTGTCT TTGTC                                                      15
```

METHODS OF INHIBITING PHAGOCYTOSIS

This is a continuation of application Ser. No. 09/158,980, filed Sep. 14, 1998, now U.S. Pat. No. 6,242,427, which is a continuation of Ser. No. 08/657,884, filed Jun. 7, 1996, now U.S. Pat. No. 5,858,981, which is a continuation-in-part of Ser. No. 08/483,530, filed Jun. 7, 1995, now abandoned, which is a continuation-in-part of Ser. No. 08/316,425, filed Sep. 30, 1994, now abandoned, which is a continuation-in-part of Ser. No. 08/129,381, filed Sep. 30, 1993, now abandoned, the entire content of which is hereby incorporated by reference in this application.

TECHNICAL FIELD

The present invention relates, in general, to methods of treating diseases resulting from interactions between immune complexes and Fc receptors. In particular, the present invention relates to methods of modulating the clearance of antibody-coated cells, viruses, or soluble antigens by inhibiting phagocytosis, and to methods of modulating the interaction of immune complexes with cellular or tissue Fc receptors. The invention also relates to the modulation of those immune reactions for which the reaction of antigen-antibody complexes with Fc receptors is an important initiating step.

BACKGROUND OF THE INVENTION

Certain immunological disorders are characterized by a disturbance in the expression of monocyte or macrophage Fc (IgG) receptors. An increase in the number of Fc receptors can result from an increase in the level of Fc receptor mediators such as gamma interferon or infection or the release of bacterial products. A decrease in the number of Fc receptors that can bind IgG can result not only from a reduction in the actual number of functional receptors but also from the saturation of Fc receptors by immune complexes. In certain autoimmune diseases, such as systemic lupus erythematosus, levels of circulating immune complexes can be high and thus receptor saturation can occur.

In autoimmune diseases, the body's mechanisms for distinguishing between itself and foreign invades malfunction. Typically, the body begins to make antibodies to certain parts of itself; these antibodies trigger the immune system which then destroys the tissue identified by the abnormal antibodies.

Autoimmune diseases have varied focal points of attack. The autoimmune hemolytic anemias represent a group of disorders in which individuals produce antibodies to one or more of their own erythrocyte membrane antigens. Coating of erythrocytes by the abnormal antibodies is followed by their clearance from the circulation by splenic macrophages and subsequent destruction in the spleen. Representative diseases in this class are immune hemolytic anemia, immune thrombocytopenic purpura and autoimmune neutropenia. Another type of autoimmune disease is the type represented by systemic lupus erythematosus and rheumatoid arthritis. In these diseases, chronic inflammation is present in the joints, tendons, kidneys, lung, heart and other organs. In rheumatoid arthritis, for example, breakdown of joint cartilage into the synovial fluid of the joint is present in later stages of the disease. In systemic lupus erythematosus, however, cartilage or bone degradation is not usually found. Systemic lupus erythematosus and rheumatoid arthritis are often present in conjunction with other types of autoimmune disease. In systemic lupus erythematosus and rheumatoid arthritis, tissue destruction is associates with the presence of IgG-containing complexes in the circulation. It is believed that recognition of these complexes in tissues by cells having Fc receptors initiates or increases tissue destruction by macrophages and possibly other cells such as polymorphonuclear leukocytes in these tissues. Reaction with these Fc receptors initiates a range of immune-associated reactions that may harm body tissues in proximity to these Fc receptor bearing cells.

Diseases that involve the interaction of IgG-containing immune complexes with macrophage Fc receptors are often treated with corticosteroids, or immunosuppressants. These treatments can have diverse and serious side effects. The present invention offers alternative treatment approaches that can be used alone or in combination with more conventional drug therapies.

SUMMARY OF THE INVENTION

It is a general object of the invention to provide a method of modulating the clearance of antibody-coated cells or immune complexes, for example, by inhibiting the phagocytic potential of cells bearing Fc receptors.

It is a specific object of the invention to provide methods of regulating the clearance of immune complexes from a mammal. In addition, it is a specific object of the invention to provide a method of inhibiting the binding of immune complexes to membrane-bound Fc receptors (and/or inhibiting ingestion of such complexes), thereby inhibiting the sequelae of undesirable tissue damage.

It is a further object of the invention to provide constructs and compounds suitable for use in the above-described methods.

In one embodiment, the present invention relates to a method of preventing the phagocytosis of immune complexes (eg IgG-containing immune complexes) and/or the release of intracellular biologically active products by cells interacting with immune complexes. An example of the present method comprises introducing into phagocytic cells of the mammal that are in contact with the immune complexes (eg, IgG-containing immune complexes) an inhibitor of a kinase endogenous to the cells that activates an Fc receptor present at the membrane of the cells.

In another embodiment, the present invention relates to a method of preventing the clearance of immune complexes (eg, IgG-containing immune complexes) from a mammal that comprises introducing into hematopoietic cells (eg phagocytic cells) of the mammal that are in contact with the immune complexes a molecule that specifically prevents Fc receptor expression at the membrane of the cells.

In a further embodiment, the present invention relates to a method of inhibiting the binding of immune complexes (eg, IgG-containing immune complexes) present in a mammal to membrane-bound Fc receptors. The method comprises introducing into the mammal a soluble Fc receptor that competes with the membrane-bound Fc receptor for binding to the immune complex. The introduction is effected under conditions such that binding of the immune complex to the membrane-bound Fc receptor is inhibited.

In yet another embodiment, the present invention relates to a method of inhibiting the phagocytic potential of a mammalian cell bearing an Fc receptor. The method comprises introducing into the cell a construct comprising, in the 5'-3' direction of transcription:

i) a promoter functional in the cell, ii) a segment of double-stranded DNA the transcribed strand of which comprises a sequence complementary to endogenous mRNA encoding the Fc receptor, and iii) a termination sequence (polyadenylation signal) functional in the cell. The construct is introduced under conditions such that the complementary strand is transcribed and binds to the endogenous mRNA thereby reducing expression of the Fc receptor and inhibiting the phagocytic potential of the cell.

Further objects and advantages of the present invention will be clear from the description that follows. It will be appreciate that the disclosure should be read in light of the teachings available in the art relating to the isolator and cloning of the classes of Fcγ receptors (FcγRI, FcγRII and Fcγ RIII) (see, for example, Allen- and Seed, Science 243:378 (1989); Hibbs et al, Proc. Natl. Acad. Sci. USA 85:2240 (1988); J. Exp. Med. 166:1668 (1987); van de Winkle et al, FASEB J., 5:A964 (1991); Brooks et al, J. Exp. Med. 170:369 (1989); Stuart et al, EMBO J. 8:3657 (1989); Qui et al, Science 248:732 (1990); Simmons and Seed, Nature 333:568 (1988); see also, Schreiber et al, Clin. Immunol. Immunopath. 62:S66 (1992).

BRIEF DESCRIPTION OF THE DRAWINGS

FIG. 3 shows tyrosine phosphorylation of the wild type and mutant γ chains by in vitro kinase assay. The γ chain was immunoprecipitated with anti-γ antisera from lysates of COS-1 transfectants. In vitro phosphorylated samples were run on a 12.5% reducing SDS-PAGE gel. The gel was treated with 1N KOH to remove phosphoserine and threonine, dried and the autoradiogram was examined after 4 days. lane 1: Sham transfectants with FcγRIIIA-α and pSVL vector without γ cDNA insert. lanes 2: FcγRIIIA α+wild type human γ. lane 3: FcγRIIIA α+wild type mouse γ. lane 4: FcγRIIIA α+M1A. lane 5: FcγRIIIA α+M2A. lane 6: FcγRIIIA α+DMA. The phosphorylated γ chains are denoted by an arrow (shown on the lower right side) The arrow with an asterisk (shown on the upper right side) is a specific tyrosine phosphoprotein band at approximately 40 kDa.

DETAILED DESCRIPTION OF THE INVENTION

Figure 1:
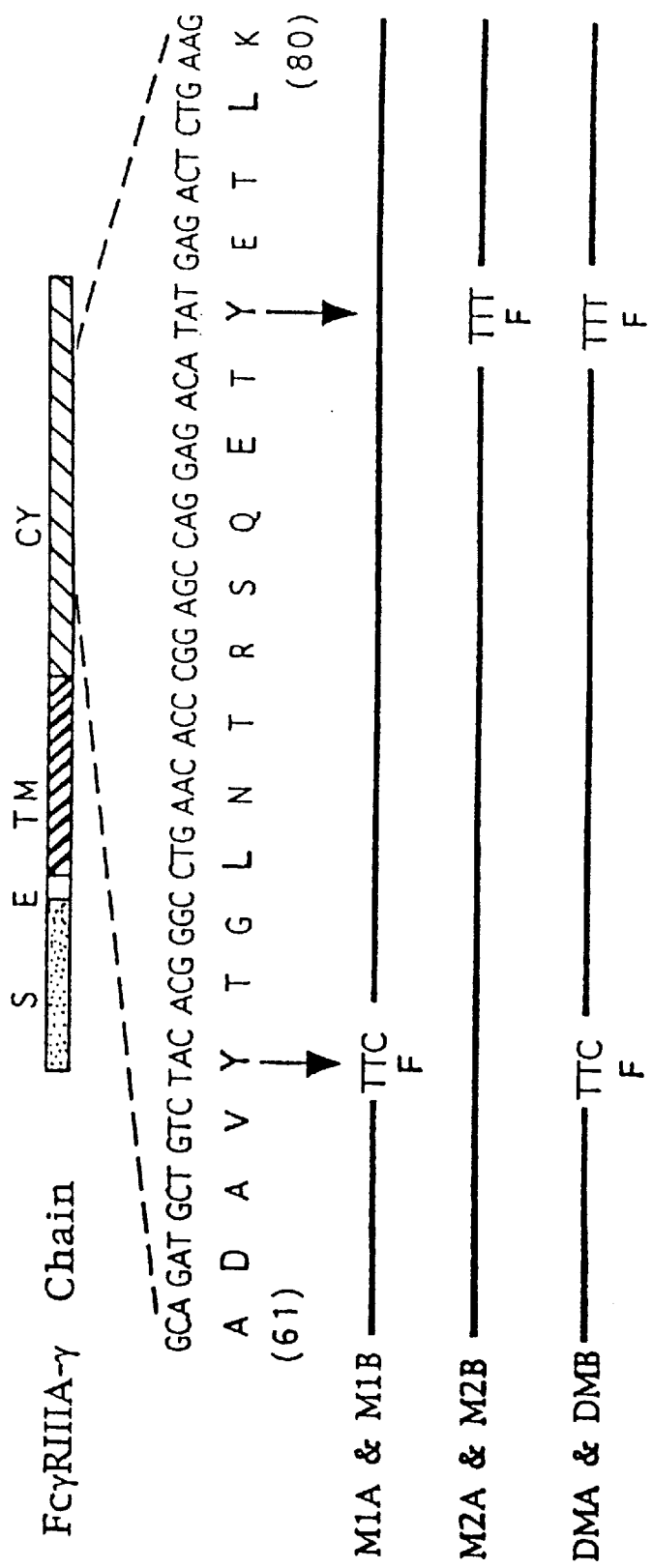
FIG. 1 shows a schematic representation of FcγRIIIA γ wild type and mutants (SEQ ID NO:1 to SEQ ID NO:5). Shown above the schematic diagram of the γ chain are signal sequence (S), external peptides (E), transmembrane domain (TM), and cytoplasmic domain (CY). The expanded area shows an area of the nucleotide sequence of the γ chain containing the conserved motif. In this Figure, the murine γ chain is shown. The conserved amino acids of the gene family of the γ and ζ chain genes are denoted by the underline. The N-proximal tyrosine encoded by the TAC codon of the nucleotides 235–237 (Ra et al, J. Biol. Chem. 264:15323 (1989)) was conservatively replaced with a phenylalanine encoded by TTC (clones M1A and M1B). Similarly, the C-proximal tyrosine encoded by TAT (168–270) was replaced with a phenylalanine encoded by TTT (clones M2A and M2B). For the double tyrosine-substitution mutants, both the N- and C-proximal tyrosines were replaced with phenylalanine (clones DMA and DMB). Solid lines of the mutants represent identical sequences to that of the wild type γ gene.
Figure 2A:
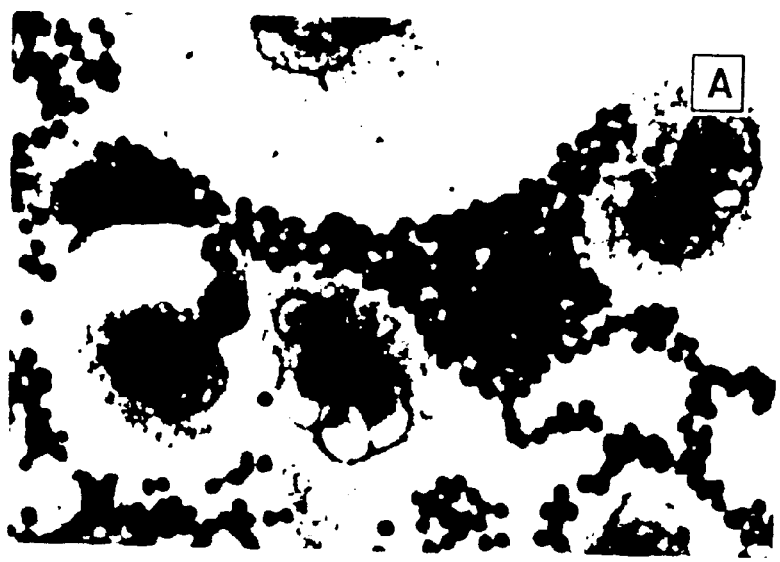
FIGS. 2A and 2B show binding and phagocytosis of IgG-sensitized RBCs (EA) by transfected COS-1 cells. Binding of EA by transfected COS-1 cells (left panel: A, C, E and G). Phagocytosis of EA by transfected COS-1 cells (right panel; B, D, F, and H). (A) and (E): binding and phagocytosis of COS-1 cells transfected with FcγRIIIA a and wild type γ. Three of the phagocytosed RBCs shown with wild type γ are marked by arrows in Figure (B), (C) and (D): transfectants containing α and γ (MIA). (E) and (F): transfectants containing α and γ (M2A). (G) and (H): transfectants containing α and γ (DMA). No phagocytosis of EA is seen in D, F and H. Pictures show images magnified by 1000×.
Figure 2B:
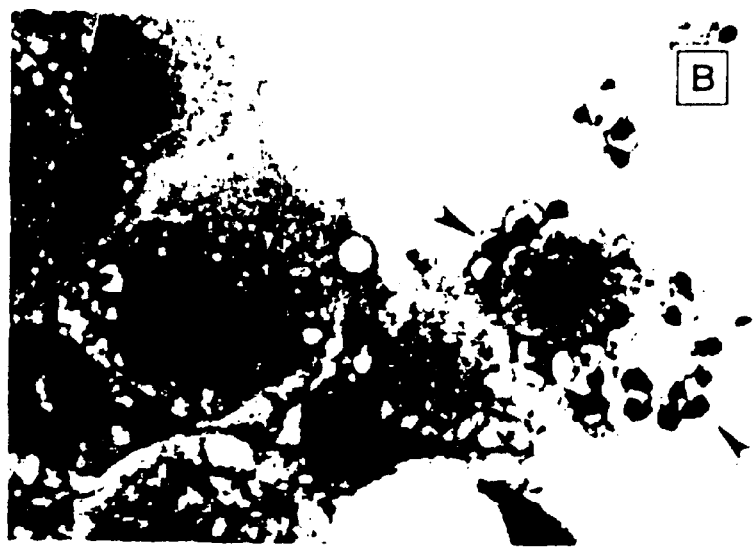
Figure 2C:
Figure 2D:
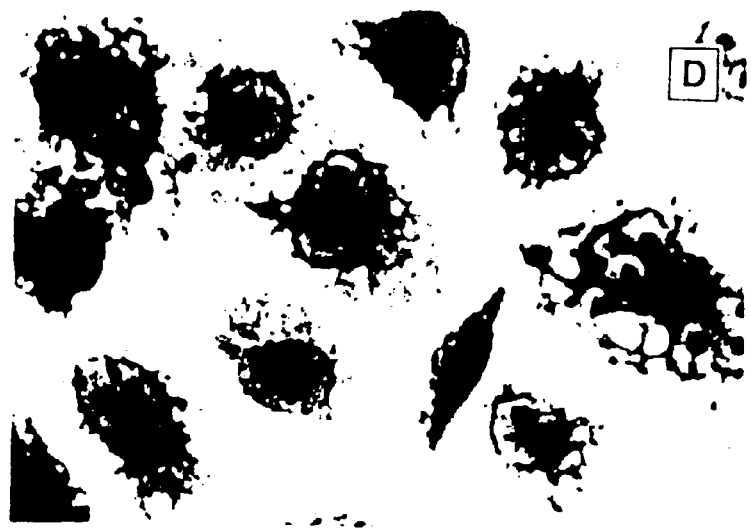
Figure 2E:
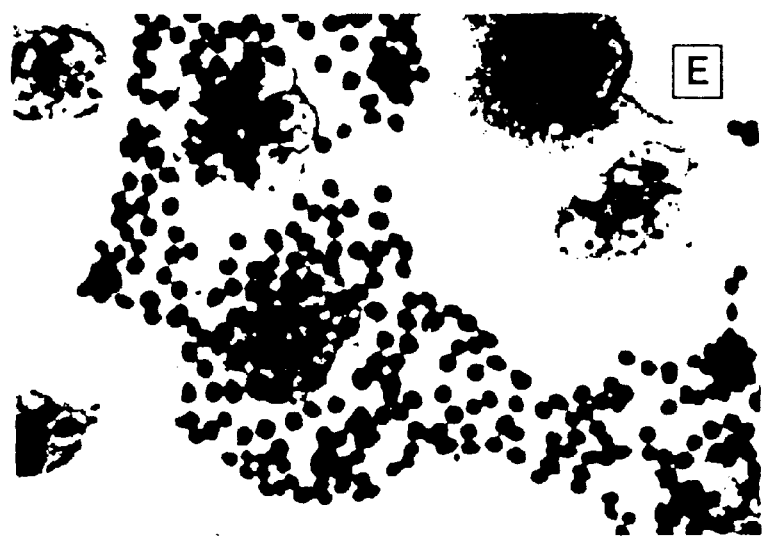
Figure 2F:
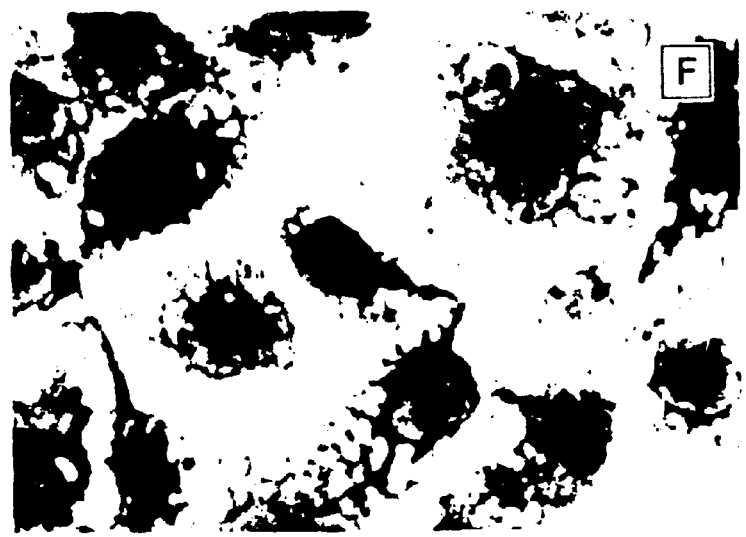
Figure 2G:
Figure 2H:
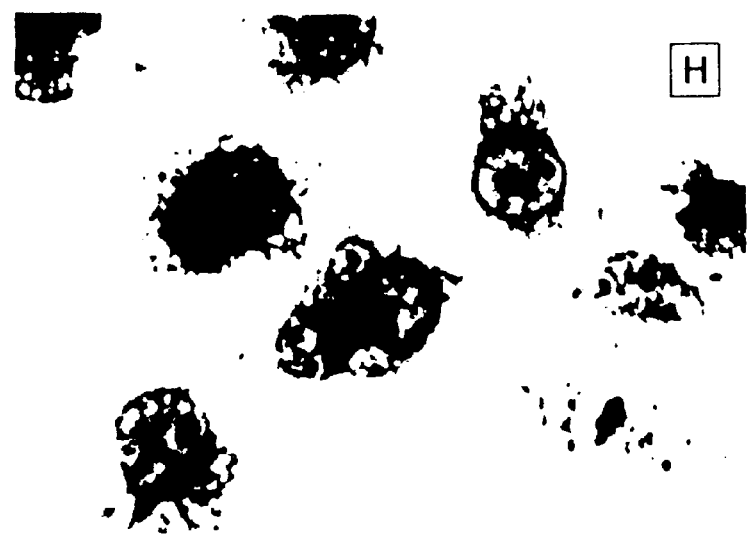
Figure 4A:
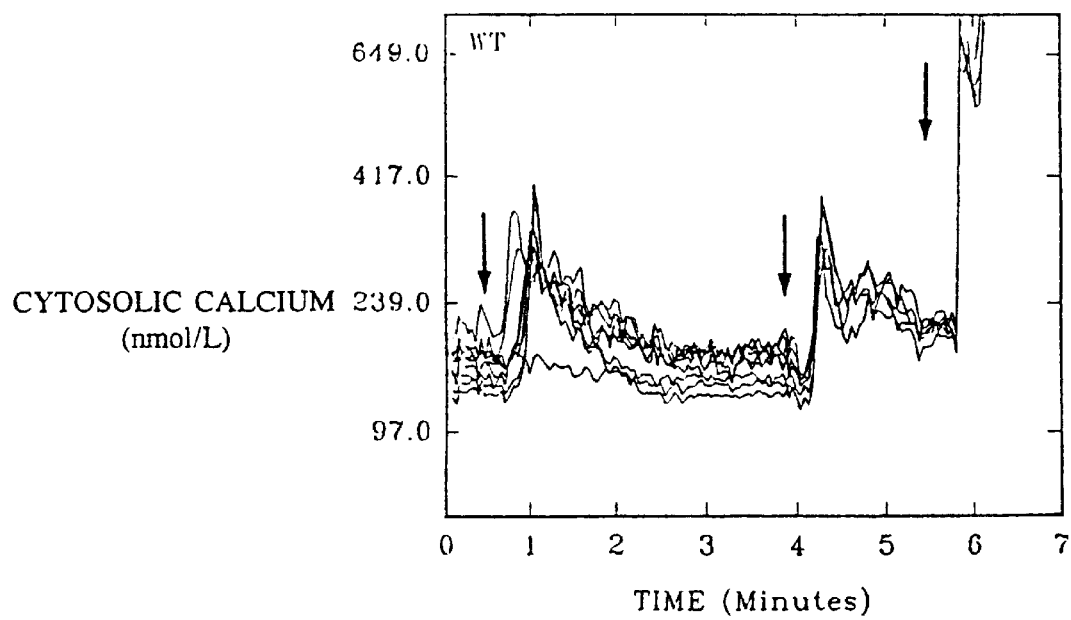
FIGS. 4A–4D are a $Ca^{2+}$ mobilization following FcγRIIIA stimulation. Measurement of $[Ca^{2+}]i$ in individual cells was carried out during crosslinking of FcγRIIIA. The time points when anti-FcγRIII mAb, epinephrine (positive control) and calcium ionophore were added are denoted by arrows in each figure. Images were acquired at either 340 or 380 nm excitation (emission=510 nm). 340/380 ratios were converted to $[Ca^{2+}]i$ based on calibration with Fura-2. The responses of M1A, M2A and DMA transfectants were greatly decreased compared to WT transfectants.
Figure 4B:
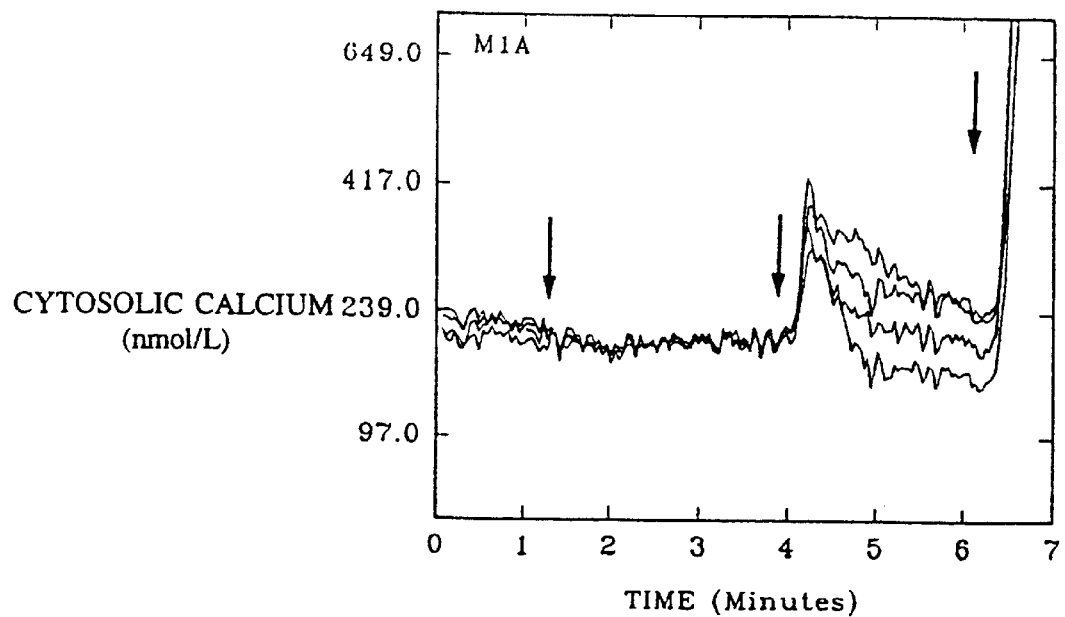
Figure 4C:
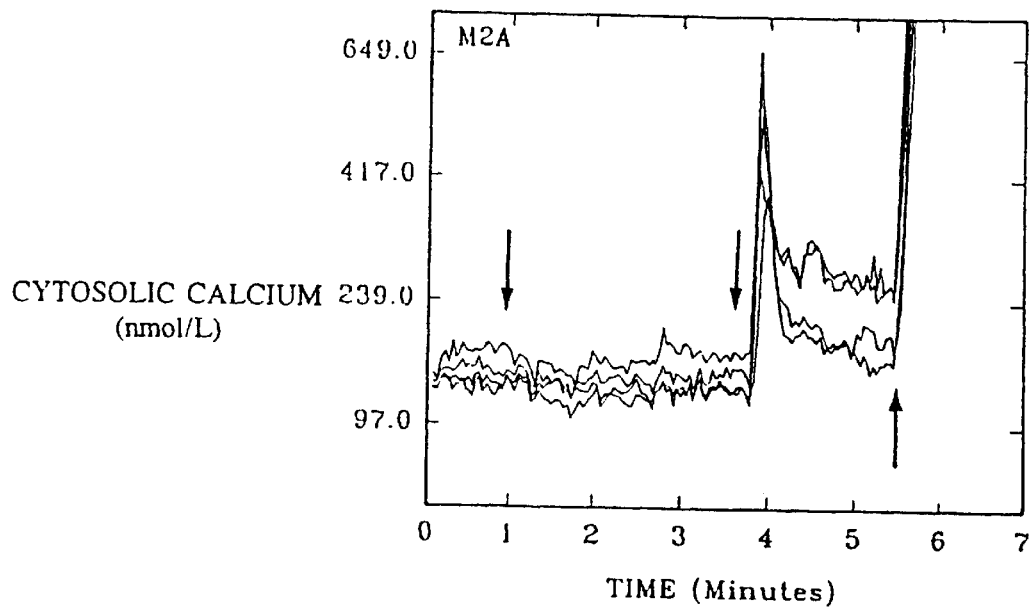
Figure 4D:
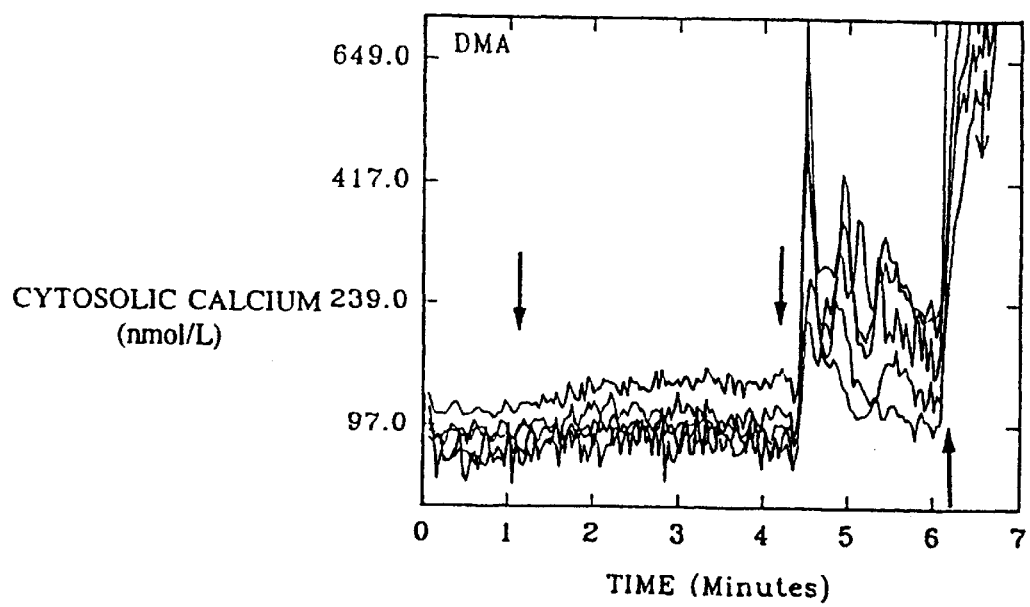

The present invention relates, at least in part, to methods of modulating the clearance from a mammal (eg, from the circulation of a mammal) of antibody-coated cells. Accordingly, the invention provides methods of treating immunologic disorders, such as autoimmune diseases, characterized by interactions of immune complexes (eg, IgG-containing immune complexes) with Fc receptors (for example, those present on the surface of macrophages), and immune mediated diseases such as asthma. The methods of the invention result in Fc receptor expression and/or function being altered so that phagocytosis of IgG antibody-coated cells is reduced. (One skilled in the art will appreciate that patients suffering from immune complex diseases such as lupus erythematosus and rheumatoid arthritis may benefit from protocols designed so as to increase clearance of circulating immune complexes in the liver and spleen and thereby prevent their deposition in tissues such as the kidney and in the joints. This increase can be effected by stimulating liver and splenic macrophages using protocols for introducing sequences encoding Fc receptors described in the commonly owned application entitled "Methods of Stimulating Phagocytosis" filed concurrently herewith, the entire disclosure of which is incorporated herein by reference.)

More specifically, the invention provides methods of inhibiting Fc receptor function by inhibiting the phosphorylation of Fc receptor components and associated molecules that are required for phagocytic signal transduction and by introducing into the circulation soluble Fc receptors that compete with the membrane bound receptor for immune complex (eg, IgG-containing immune complex) binding. The invention also provides a method of inhibiting expression of Fc receptors by introducing into receptor-producing cells Fc receptor antisense constructs. The invention also provides methods of degrading Fc receptor RNA using, for example, ribozymes.

Inhibition of Fc Receptor Mediated Signal Transduction Events:

In one embodiment, the present invention relates to a method of preventing ingestion (eg phagocytosis) of immune complexes (eg IgG-coated cells) by inhibiting phosphorylation of core sequences within the cytoplasmic domain of Fc receptors. Phosphorylation of cytoplasmic residues of FcγRIIA and the γ subunit of FcγRIIIA has been shown to be essential for signal transduction events involved in phagocytosis (Indik et al, Trans. Ass. Amer. Phys, 105:214 (1992); Park et al, Clin. Res. 41:324A (1993); Darby et al, Blood 79:352A (1992); Mitchell et al, Clin. Res. 41:189A (1993); Huang et al, J. Biol, Chem. 267:5467 (1992); Hunter et al, Clin. Res. 41:244A (1993); Park et al, J. Clin. Invest. 92:2073 (1993)). More specifically, phosphorylation of tyrosine residues present within the motif E-X8-D-X2-Y-X2-L-X12-Y-X2-L (SEQ ID NO:6), present in the cytoplasmic domain of FcγRIIA, and the motif D/E-X2,7-D/E-Y-x2-L-X7-Y-X2-L (SEQ ID NO:7), present in the cytoplasmic domains of the γ and ( chains of FcγRIIIA, is required for phagocytic signal transduction (the numbers following the letter X denote the number of amino acids at that position; X can be any amino acid but X2 within a Y-X2-L (SEQ ID NO:8) is preferably the amino acids present in a Y-X2-L sequence of the cytoplasmic domain of FcγRIIA or the γ chain of FcγRIII). It appears that the second Y-X2-L of these core sequences (motifs) is particularly important for phagocytosis. The present invention contemplates the introduction into target cells of an inhibitor of the kinase(s) responsible for phosphorylation. In a specific embodiment, the inhibitor is a peptide that includes a sequence similar to, if not identical to, at least a functional portion of a tyrosine-containing motif (note, for example, the underlined portions of the motifs set forth above) and thus serves as a competitive inhibitor of the kinase(s). As an example, the inhibitor can take the form of an Fc receptor devoid of the extracellular domain or devoid of the extracellular and transmembrane domains. Alternatively, the inhibitor can be structurally distinct from the above motifs, or functional portions thereof, and can inhibit phosphorylation competitively or non-competitively (eg, a mimetic of the active peptide can be used having a structural conformation similar to the binding site of the active peptide). For mast cells, or mother Fcε receptor bearing cells (eg macrophages), the sequences of the γ chain of FcεRI necessary for mediator release (eg, histamine, cytokines and leukotrienes) can be inhibited using this strategy.

The peptide inhibitor of the invention, or mimetic thereof, can be introduced into target cells directly, for example, using liposomes. (See also approaches described in Science 26:1877 (1993) for administration of peptides modified so as to render them capable of crossing cellular lipid membranes.) Alternatively, a DNA sequence encoding the peptide inhibitor can be introduced using gene therapy protocols so that the peptide is produced intracellularly.

The inhibitor or inhibitor encoding sequence can be administered to the cells of the lung, including macrophages, in the form of an aerosol. The inhibitor or inhibitor encoding sequence can be present in the aerosol as a particle (e.g. liposome, or non-infectious bacteria, for example, Listeria in the case of the encoding sequence) that is phagocytosed by the pulmonary macrophages. Phagocytosis results in the introduction into the macrophages of the inhibitor or inhibitor encoding sequence. Viral vectors can also be used to introduce the peptide inhibitor encoding sequence of the invention into cells of the pulmonary tree. The vectors can be introduced as an aerosol and can take the form of a replication defective herpes or adenoviral vector. Retroviral vectors can also be used. (See, generally, Bajocchi et al, Nat. Genet. 3:229 (1993); Lemarchand et al, Circ. Res., 72:1132 (1993); Ram et al, Cancer Res. 53:83 (1993); Crystal, Am. J. Med. 92:445 (1992); Yoshimura et al, Nucl. Acids Res. 20:3233 (1992); Morecki et al, Cancer Immunol. Immunother. 32:342 (1991); Culver et al, Hum. Gene Ther. 1:399 (1990); Culver et al, Transplant. Proc., 23:170 (1991).)

Blood monocytes can be transformed (infected) ex vivo with the peptide inhibitor encoding sequence of the invention and then reintroduced into the patient so that the inhibitor is produced in vivo.

An alternative approach to inhibiting phosphorylation involves the use of ribozymes that recognize RNA sequences specifying Fc receptor phosphorylation sites (eg, in FcγRIIA and/or in the γ subunit of FcγRIIIA), as well as RNA sequences specifying enzyme active sites. Introduction of the ribozyme can be effected using a carrier such as a liposome coated with IgG so as to direct insertion to Fcγ receptor bearing cells. Alternatively, IgE-coated liposomes car be used to direct the ribozyme to mast cells or basophiles, or other cells bearing the IgE receptor FcεRI with its associated γ subunit. One skilled in the art will appreciate that this is an approach suitable for use in treating allergic disorders. The γ subunit of the IgE receptor is responsible for transmitting the signal inducing the release of intracellular mediators by Fcε receptor bearing cells such as mast cells. The destruction of the γ chain RNA is predicted to inhibit the release of these bioactive products.

In accordance with the above approach, ribozymes administered as described would bind to a few selected sequences (eg, RNA splicing and 5' untranslated sequences for which they were specific, for example, in FcγRIIA RNA or FcγRIIIA γ chain RNA) and the enzymatic activity associated with the ribozyme would result in digestion and thus removal of the RNA specifying functional sequences of the receptor necessary for phagocytic signal transduction. RNA sequences specifying the sequences of the γ chain of FcεRI necessary for mediator release (eg, histamine, cytokines and leukotrienes) can be eliminated using this strategy.

Where advantageous, continuous in vivo production of the ribozyme can be effected using ex vivo constructed packaging cells (eg, Psi2-like cells; see Miller and Rosman, Biotechniques 7:980, 1989 and Current Protocols in Molecular Biology III:9.1, 1992 (Supp. 17)). One skilled in the art will appreciate that a suicide gene can be included in such a cell so that ribozyme production can be terminated.

A further approach to inhibiting receptor phosphorylation involves the use of a ribozyme or any antisense construct that targets Syk encoding sequences (see Example V). The Syk gene product, but not the gene product of ZAP-70 of the Syk kinase family, has been shown to stimulate FcγRI and FcγRIIIA phagocytosis mediated by both the γ and ζ chains. (ZAP-70 in the presence of certain Src related tyrosine kinases can stimulate FcγRI and FcγRIIIA phagocytosis.) Thus, by targeting Syk sequences, inhibition of Syk expression and dependent phosphorylation can be effected. Constructs and ribozymes suitable for use in this method can be readily selected by one skilled in the art (see Yagi et al, Biochem. Biophys. Res. Comm. 200:28 (1994), Law et al, J. Biol. Chem. 269:12310 (1994) for Syk gene sequence).

Figure 11:
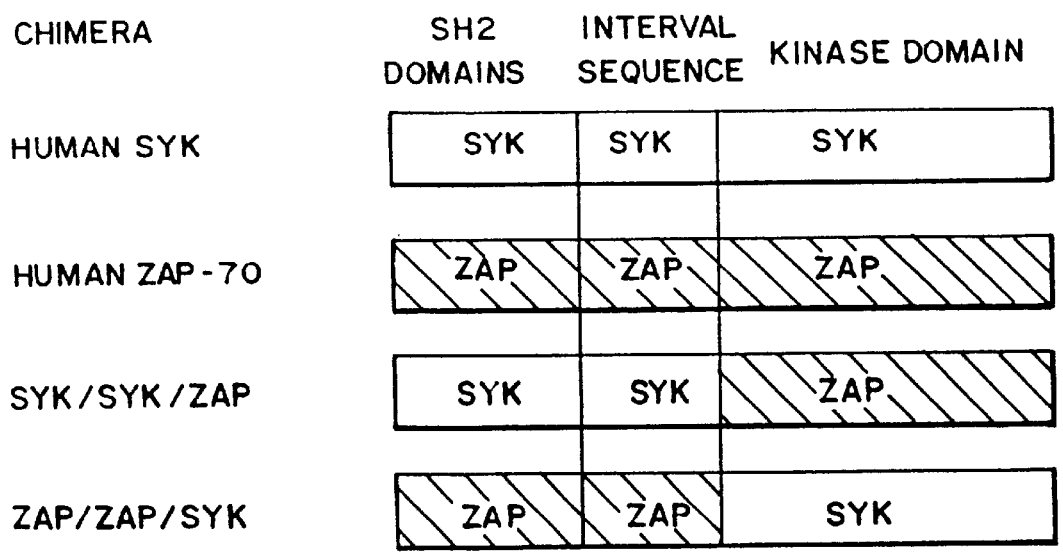
FIG. 11. Structure of human Syk/ZAP-70 chimeras.

Chimeras of Syk and ZAP-70 have been used to determine the sequence responsible for differences signaling between Syk and ZAP-70. A ZAP-70 mutant which the ZAP-70 SH2 domains and the ZAP-70 interval region between the second SH2 domain and the catalytic domain have been replaced with the Syk SH2 domains and interval region (FIG. 11). The studies indicate that this chimera acts like Syk in that it enhances the Fcγ receptor mediated phagocytic signaling. In parallel, a Syk kinase mutant has been constructed in which the Syk SH2 domains and the Syk interval region have been replaced with the ZAP-70 SH2 domains and interval region. This chimera acts like ZAP-70 in that it does not increase Fcγ receptor mediated signaling (COS-1 cell transfectants and phagocytic signaling are one readout). Further chimeras of Syk and ZAP-70 have been produced. A Syk mutant has been constructed in which the SH$_2$ domain has been replaced with the SH2 domain of ZAP-70. This chimera acts like Syk kinase. Similarly, a ZAP-70 mutant has been constructed in which the SH2 domain has been replaced with the SH2 domain of Syk kinase. This chimera acts like ZAP-70. A Syk mutant has been constructed in which the interval region between the second SH2 domain and the catalytic (kinase) domain has been replaced with the interval region of ZAP-70. This chimera acts like ZAP-70. Similarly, a ZAP-70 mutant has been constructed in which the interval region of ZAP-70 has been replaced with the interval region of Syk kinase. This chimera acts like Syk kinase. These experiments with chimeras of Syk and ZAP-70 indicate that the sequences in the interval region between the second SH2 domain and the catalytic (kinase) domain are responsible for the ability of Syk to interact with Fcγ receptor signaling. (See Park and Schreiber, Proc. Natl. Acad. Sci. USA 92:7381 (1995) and references cited therein for region/domain description). Chimeras were produced overlap PCR using wild type Syk and ZAP-70.)

The identification of the interval sequence of Syk kinase as being responsible for signal transduction events, including those involved in phagocytosis, makes possible a screen that can be used to test compounds (eg peptides or mimetics) for their ability to selectively inhibit such events. For example, a test compound can be contacted with a polypeptide comprising the Syk interval region, or portion thereof of at least 3, 5 or 7 amino acids or larger portions, for example, of at least 20, 50 or 100 amino acids (eg a chimera comprising the ZAP-70 SH2 and kinase domains and the Syk interval sequence), and a polypeptide comprising the ZAP-70 interval region (eg a chimera comprising the Syk SH2 and kinase domains and the ZAP-70 interval sequence). Compounds that bind the former polypeptide but not the latter are putative selective inhibitors of signaling events mediated by Syk interval sequences (including phagocytosis and mediator release from mast cells and other Fcε receptor bearing cells). Such compounds can also be tested by introducing into Syk-deficient, potentially phagocytic cells (eg Fcγ receptor bearing cells, including COS cells bearing an Fcγ receptor) a construct encoding a polypeptide comprising the Syk interval sequence (eg a construct encoding the chimera described above), contacting that cell with the test compound and assaying for the ability of the cell to carry out phagocytosis; phagocytosis being a readout for signaling by Syk kinase. Compounds that inhibit phagocytosis can he expected to inhibit other signaling events mediated by Syk interval region sequences. Compounds that inhibit the phagocytic potential of the cells expressing the Syk interval region can then be tested for stability, toxicity, etc in accordance with standard protocols. This approach can also be used to screen for compounds (eg peptides or mimetics) that inhibit mast cell, or other Fcε receptor bearing cell, mediator release (eg histamine release).

Peptides and mimetics identified using the above-described screen, or otherwise identified, can be formulated as pharmaceutical compositions and administered, for example, systemically or directly to the lung (eg via an aerosol). Delivery can be effected using techniques described herein. Optimum dosing can be readily determined. The Syk interval sequence (eg between the second SH2 domain and the catalytic (kinase) domain) (eg in purified or isolated form) or portion thereof of at least 5 or 6 amino acids, or mimetics thereof, are within the scope of the invention and can be formulated and used as described above.

As discussed below, the present invention also contemplates the use of Syk antisense constructs to inhibit mediator (eg histamine) release from cells bearing an Fcε receptor, such as mast cells (see Example VI). Inhibition of histamine (a mast cell mediator) release, for example, is of therapeutic importance in the treatment of asthma. Preferred targets of Syk antisense constructs are described below (see also Examples V and VI). The constructs can be administered systemically or directly to the lung (eg aerosol administration). Delivery can be effected using the techniques described herein (including liposome formulations). Optimum dosing will depend on the patient, and the construct and mode of administration used.

Soluble Fc Receptors:

In a further embodiment, the present invention relates to a method of inhibiting the interaction between immune complexes (eg, IgG-containing immune complexes) and membrane-associated Fc receptors and thereby suppressing the clearance of such complexes by phagocytosis (alternatively, the signalling through the Fc receptor resulting in the release of intracellular mediators). The method involves introducing into the circulation a soluble form of the Fc receptor that competes with the membrane bound form for immune complex binding. Transcripts of certain soluble forms have been identified in cells of megakaryocytic and monocyte/myeloid lineages (Rappaport et al, Exp. Hemotol. 21:689 (1993); Warmerdam et al, J. Exp. Med. 172:19 (1990)). These transcripts lack sequences coding for the transmembrane receptor reason but retain sequences coding for the cytoplasmic domain. The present invention contemplates the production and use of soluble Fc receptors that include an extracellular domain alone or in combination with a cytoplasmic domain. Suitable receptors are capable of competing with membrane bound Fc receptors for binding of IgG-coated cells.

Soluble receptors of the invention can take the form of FcγRI, FcγRII or FcγRIII extracellular domains alone or binding portions thereof (alternatively, a soluble receptor of FcεRI can be employed taking the form of an extracellular domain alone or binding portion thereof). As noted above, cytoplasmic domains, or portions thereof, can also be present. The following are examples of possible soluble receptors where the "I" and "IIA" correspond to FcγRI and FcγRIIA, respectively, and where α and γ correspond to the α and γ chains of FcγRIII, the first designation indicating the source of the extracellular domain and the second the source of the cytoplasmic domain: I:I, I, IIA, IIA:IIA, I:IIA, α:γ, α, α:IIA, I:γ.

Soluble receptors, depending on their nature, can be prepared chemically or recombinantly (Horton et al, Biotechniques 8:528 (1990)). The soluble receptors can be administered systemically or to the lung as described above in connection with inhibitors of receptor phosphorylation. When in vivo synthesis of soluble receptors from sequences encoding same is to be effected, such sequences are inserted into appropriate vectors (see above) and operably linked to regulatory sequences functional in the target cell.

Antisense Constructs:

In a further embodiment, the present invention relates to a method of inhibiting Fc receptor expression in mammalian host cells by introducing into such cells an antisense construct comprising, in the 5'-3' direction of transcription: i) a promoter functional in the cells, ii) a segment of double-stranded DNA, the transcribed strand of which includes a sequence complementary to the endogenous MRNA of the Fc receptor the expression of which is to be inhibited, and iii) a termination sequence functional in the host cells. This embodiment of the invention makes it possible to regulate the expression of a specific Fc receptor in cells producing multiple receptor classes. This specificity can be achieved by selecting for inclusion in the DNA segment ((ii) above) sequences unique to the mRNA of the endogenous Fc receptor.

As indicated above, the invention also relates to antisense constructs that target Syk kinase encoding sequences. In such constructs, (ii) above is a segment of double-stranded DNA, the transcribed strand of which includes a sequence complementary to endogeneous mRNA of Syk kinase.

Factors that affect the efficacy of antisense oligonucleotides include stability of the antisense oligonucleotides, their delivery into the cell cytoplasm, and their accessibility to the target mRNA. Syk antisense oligonucleotides of the present invention are modified in three steps to address these issues. First, phosphodiester links at the 5' or 3' terminus, preferably both, are modified, for example, with phosphorothioates. Second, a stem-loop structure is used to protect the antisense sequence in the loop domain from nucleases. The stem has complementary terminal sequences, for example, with only Gs and Cs. The loop domain has, for example, three antisense sequences targeting different sites of Syk mRNA. mRNA forms secondary structures by intramoluclear hybridization, and mRNA secondary structures may inhibit access of antisense oligonucleotides to target sequences. To identify sequences with "open" structures that provide better access for antisense oligonucleotides, the entire Syk MRNA sequence was scanned with an RNA secondary-structure predication program. Syk mRNA was scanned in three staggered frames, and the most "open" sequences with minimum secondary structures were chosen. Stem-loop antisense oligonucleotide reduced the phogocytic signal more dramatically than a mixture of three linear antisense oligonucleotides. The higher efficacy of the stem-loop Syk antisense oligonucleotide may be due to better stability from nuclease digestion. Third, Syk antisense oligonucleotides were also complexed, for example, with cationic liposomes, to improve delivery to the cells. The stability of the stem-loop Syk antisense oligonucleotides markedly improved when complexed with liposomes. A stem-loop antisense oligonucleotide directed at, for example, the FcγRIIIA γ subunit mRNA has also be used. With the use of peripheral blood monocytes and the stem-loop γ-chain antisense oligonucleotide, the monocyte γ-chain message, assessed by RT-PCR, was decreased by >80%. Liposomes can be delivered to the reticuloendothelial system, for which monocytes/macrophages are a major residential cell population. The complex of liposome-stem-loop Syk antisense oligonucleotide is advantageous for use as a therapeutic agent(s) for immunologic disorders requiring down-regulation of Fcγ receptor-mediated function in monocytes/macrophages. Syk kinase is also associated with FcεRI and with the B-cell antigen receptor. The stem-loop Syk antisense oligonucleotide is also useful for investigating intracellular signaling events through these receptors and for developing therapeutic agents to modulate the signals mediated by these receptors.

In accordance with the antisense embodiment of the present invention, the sequence complementary to the endogenous mRNA target is a least 15 nucleotides in length, preferably, at leas: 30 and, most preferably, at least 50. The sequence typically less than 5000 nucleotides in length, preferably less than 2000, and most preferably less than 1000. The sequence can be complementary to a translated or untranslated region of the target mRNA (see, for example, McKenzie et al, Molec. Immunol. 29:1165 (1992), Masuda et al, Mol. Biol. Cell 7: in press, July (1996)). Both the length of the antisense sequence and the mRNA site to which it binds can vary depending on the nature of the antisense sequence, the mRNA site and the degree of inhibition sought. Optimization of these parameters can be effected without undue experimentation.

Appropriate regulatory sequences and vectors can be selected from those known in the art.

Administration of the antisense construct, for example, to the lung and to the spleen, can be carried out as described above using both in vivo and ex vivo transformation protocols. One skilled in the art will appreciate that the antisense transcript itself can be introduced directly into the target cells using methods known in the art, including those described above (see also Example V—there, linear and stem-loop Syk antisense oligonucleotides (ODNs) modified with phosphorothioate show partial resistance to serum nucleases. When complexed with liposomes, antisense ODNs with phosphorothioate modifications at 5' and 3' termini are even more stable. Stem-loop Syk antisense ODN with phosphorothioate modifications exhibit exceptional stability in serum).

In addition to the above approaches for inhibiting phagocytosis, the present invention also relates to a method of effecting inhibition by introducing into a cell having phagocytic potential FcγRIIB (eg FcγRIIB2), which is capable of inhibiting the function of Fcγ receptors, including FcγRIIA (Hunter et al, FASFB J. June 1996, New Orleans, La.). Introduction of FcγRIIB can be effected by transfecting/infecting a target cell with a construct comprising a sequence encoding FcγRIIB, or portion thereof that effects the inhibition (Brooks et al, J. Exp. Med. 170:1369 (1989); Indik et al, Blood 83:2072 (1994)). Suitable constructs can be selected by one skilled in the art.

The following non-limiting Examples describe certain aspects of the invention in greater detail.

EXAMPLE I

Production of Recombinant Soluble FcγRIII

Recombinant soluble FcγRIII proteins can be produced using expression vectors as described below. The soluble protein can correspond to FcγRIII with the transmembrane domain removed. The constructs can be introduced into mammalian cells under conditions such that expression of the receptor encoding sequence occurs. The recombinant proteins thus produced are isolated both from the cell lysates and from the supernatants.

Transfection of adherent cells or cells in suspension:

Transfection of adherent cells, eg, CHO cells or COS cells, or an appropriate suspension cell system will be performed. Permanent transfectants expressing soluble forms of Fcγ receptor will be established by electroporation, calcium phosphate or other established methods. Transfected cells will be allowed to grow 48 hours and selected in media containing Geneticin at 2 mg/ml (Gibco BRL, Gaithersburg, Md.) or other selection drug. After approximately twelve weeks, positive colonies will be isolated and expanded for further characterization of the clones. The isolated clones will be examined by enzyme-linked immunoassay (ELISA) using ELISA plates (Dynatech, Alexandria, Va.) to select a transfectant cell line expression the highest quantity of the soluble receptor. Mass culture of adherent transfectants will be achieved by employing the hollow-fiber tissue culture system.

EXAMPLE II

Function of Soluble FcγRIII

The functions of soluble FcγRIII proteins are assessed both in vitro and in vivo. The effect of soluble Fc receptors on IgG-immune complex binding to cellular membrane-bound receptors depends on several factors including the local concentrations of the ligand and soluble receptor, the surface density of the membrane-bound receptor, the valence of the ligand and the relative affinities of the two receptor forms for ligand. The limiting factors in the interaction of soluble FcγRIII receptors with ligand and cellular membranes can be deciphered using available model systems.

The in vitro assay systems rely on the competition of soluble receptors with cell membrane receptors for labeled IgG ligand and IgG-coated erythrocytes (EA). Fcγ receptor-negative cells are transfected with transmembrane FcγRIII molecules that retain the functional capacity to bind and ingest IgG-containing immune complexes and antibody-coated cells (Ruiz and Schreiber, J. Clin. Invest. 88:149 (1991)). These assays are used to examine the function of soluble receptors and the ability of soluble receptors to interfere with membrane receptor detection of both EA and oligomeric forms of IgG. The function of soluble FcγRIII is also examined in vivo. In these studies, an established experimental animal model is used to study whether soluble FcγRIII administered in vivo alters the clearance of antibody coated cells (Ruiz and Schreiber, J. Clin. Invest. 88:149 (1991)). The immunoregulatory potential of soluble FcγRIII is examined in this manner.

EXAMPLE III

Cytoplasmic Tyrosine Residues Required For Phagocytic Signal Mediation

Experimental Protocols:

Plasmid construction and introduction of point mutations:

The pSVL eucaryotic expression vector (Pharmacia LKB, Piscataway, N.J.) was employed for expression of FcγRIIIA in COS-1 cells. huFcγRIIIA α cDNA was cloned into the XbaI and BamHI cloning sites of pSVL. Similarly, muFcγRIIIA γ cDNA was cloned into XhoI and BamHI cloning sites. TCR/FcγRIIIA ζ was cloned into the XbaI and BamHI cloning sites of pSVL. Conservative replacement of cytoplasmic tyrosines of the γ chain by phenylalanine was achieved using the two step overlap-extension polymerase chain reaction (PCR) (Horton et al, Biotechniques 8:528 (1990)). Double tyrosine substitution mutants were constructed sequentially by the substitution of the N-terminal tyrosine-residue followed by the substitution of the C-terminal tyrosine residue. Six clones from each mutant were isolated and subjected to DNA sequencing. Two clones from each tyrosine substitution were randomly selected for further studies from several clones with correct DNA sequence.

Transient transfection:

FcγRIIIA isoforms, FcγRIIIA-γγ, FcγRIIIA-ζζ, were generated by cotransfection of COS-1 cells with cDNA of γ or ζ as well as cDNA of α. Transfections of cDNAs were carried out with a modified DEAE-Dextran method. Briefly, 300,000 COS-1 cells were seeded on 35 mm well plates 24 hours prior to transfection. Plates of 70 to 80% confluence were washed twice and incubated for 30 minutes with Dulbeco's Modification of Eagle's Medium (DMEM, Gibco BRL, Grand Island, N.Y.) before transfection. Four µg of plasmid DNA (0.5 µg/µl) was slowly added to 1 ml of a transfection buffer containing Nu medium (DMEM with 10% of NuSerum [Collaborative Biomedical, Two Oak Park, Bedford, Mass.], 1 mg/ml of DEAE Dextran and 100 µM chloroquine. The transfection buffer containing DNA was added to COS-1 cells with incubation for 4 hours at 37° C. Cells were then shocked with 10% DMSO in phosphate buffered saline (PBS) for 2 minutes, washed twice with DMEM and grown in NuSerum supplemented DMEM. Cells were studied 48 hours following transfection.

Immunofluorescence staining and flow cytofluorimetry: Transfected cells were harvested with staining buffer (PBS containing 0.02 a sodium azide and 0.1%. BSA) using transfer pipettes. Cells were centrifuged, resuspended in 60 µl of staining buffer and incubated with either the anti-FcγRIII mAb, 3G8 (Unkeless et al, Annu. Rev. Immunol. 6:251 (1988)), or an isotype control for 30 minutes at 4° C. Cells were washed and stained with fluorescein-conjugated goat anti-mouse IgG (Tago Inc. Burlingame, Calif.). The stained cells were examined using a FACStar flowcytometer (Becton Dickinson Co., Mountain View, Calif.).

Binding and phagocytosis of IgG-sensitized RBCs (EA): Sterile sheep red blood cells ($10^9$/ml) in calcium and magnesium-free PBS were sensitized by incubation with an equal volume of a subagglutinating titer of rabbit anti-sheep RBC antibody (Cappel Laboratories, Cochranville, Pa.). The IgG-sensitized RBCs (EA) were washed twice with PBS and resuspended to a final concentration of $10^9$/ml for overlaying on transfected COS-1 cells. Cells were examined for resetting (>10 EA per COS-1 cell) and phagocytosis as described previously (Indik et al, J. Clin. Invest. 88:A66 (1991)). For the analysis of phagocytosis, COS-1 cells bound with EA (after three washings) were subjected to a brief hypotonic shock (35 seconds) with hypotonic PBS to remove surface bound EA. The cells were then stained with Wright-Giemsa staining solutions, and phagocytosis (ingested EA) was determined by light microscopy. Results obtained were analyzed by Student's T-test.

In vitro kinase assay:
Transfected cells (2×10 cells) were washed once with PBS and incubated sequentially on ice with 5 µg/ml each of anti-FcγRIII mAb and goat anti-mouse IgG for 10 minutes. Cells were washed once with PBS and incubated at room temperature for 3 minutes before adding 1.5 ml of lysis buffer (150 mM NaCl, 25 mM Hepes [pH 7.4] and 1%. polyoxyethylene 10 oleyl ether [BRIJ-96; Sigma, St. Louis, Mo.]) containing phosphatase and protease inhibitors. Inhibitors of phosphatases and proteases (1 mM EGTA, 1 mM Na orthovanadate, 1 mM PMSF 10 µg/ml aprotinin, 50 µg/ml leupeptin, and 100 µg/ml soybean trysin inhibitor) were added fresh to lysis buffer. After 15 minutes of lysis on ice, cell lysates were centrifuged for 30 minutes at 4° C. to clarify. The FcγRIIIA-γ chain was immunoprecipitated with anti-human γ antiserum (provided by Jean-Pierre Kinet, NIAID-NIH, Rockville, Md.) and Protein A-sepharose CL4B (Signa, St. Louis, Mo.) in lysis buffer. Pellets were washed three times in lysis buffer and once in low salt buffer (100 mM NaCl, 25 mM Hepes, pH 7.4 and 5 mM $MnCl_2$). Pellets were incubated (20° C., 10 min.) with 30 µl of a mixture containing 25 mM Hepes, pH 7.4, 5 mM $MnCl_2$, 5 mm p-nitrophenyl-phosphate, 1 µM cold ATP (Boehringer Mannheim, Indianapolis, Ind.) and 5 µCiγ-[$^{32}$P]ATP (6000 Ci or 222 TBq/mmol; Dupont NEN, Boston, Mass.). Reactions were stopped by adding reducing SDS-PAGE sample buffer and labelled proteins were separated on a 12.5% reducing SDS-PAGE gel. The gel was fixed in methanol/acetic acid, treated with 1 N KOH (2 hrs at 55° C.) to remove phosphoserine and threonine, dried and autoradiogrammed for 4 days.

[$Ca^{2+}$]i Mobilization:
COS-1 cells plated on glass coverslips were incubated with 2 µM Fura-2/AM (Calbiochem. San Diego, Calif.) for 30 minutes, washed twice and the coverslips then transferred to a Leidem cell chamber (Medical Systems, Greenville, N.Y.) for multiple single-cell measurements of [$Ca^{2+}$]i. FcγRIIIA receptors were crosslinked either with biotinylated anti-FcγRIII followed by the addition of streptavidin or with anti-FcγRTII mAB 3G8 whole IgG. As a positive control, 10 µM epinephrine was added to crosslink epinephrine receptors expressed on COS cells. Calcium imaging was performed using a 40×fluorescence objective on a Nikon Diaphot microscope with the image-1 AT quantitative fluorescence system (Universal Imaging, West Chester, Pa.). Images were acquired at either 340 or 380 nm excitation (emission=510 nm) 340/380 ratio images were calculated on a pixel by pixel basis and the average 340/380 ratio within each cell determined at each time point. 340/380 ratios were converted to [$Ca^+$]i based on solution calibration using free Fura-2 acid.

Phagocytosis Mediated by FcγRIIIA α and Associated γ and ζ Chains:

Wild type γ and ζ cDNAs of FcγRIIIA were cotransfected with the FcγRIIIA-α chain into COS-1 cells to examine their ability to induce phagocytosis of EA (sensitized RBC). Surface expression or FcγRIIIA was determined by flow cytometry and was equally efficient in cotransfection with either γ or ζ (Table 1). The mean fluorescence intensity (FMI) for cotransfected cells stained with anti-FcγRIII mAB increased by 15 fold compared to cells stained with an IgG isotype control or compared to mock-transfected cells stained with anti-FcγRIII mAB (Table I). The transfectants were examined for their ability to bind and phagocytose IgG sensitized RBCs (EA). Approximately 500 of COS-1 transfectants avidly bound EA (Table 1). Microscopic examination of COS-1 cells transfected with wild type γ consistently showed the ingestion of EA by 20±5% of the cells examined (p<9.02) Thus, phagocytosis of EA was detected in approximately 40% of COS-1 cell transfectants that bound EA. In contrast, cotransfectants containing the ζ chain revealed 3.8% of cells with ingested EA (p<0.02) (Table 1). Moreover, in ζ-containing cells which demonstrated phagocytosis the average number of ingested EA per cell was reduced to less than one half the level of that observed with γ. COS-1 cells transfected with all three cDNAs, α, γ, and ζ, revealed 16% cells with ingested EA, showing consistent attenuation in phagocytosis (Table 1). In contrast, neither sham transfectants with EA nor transfectants with E (non-sensitized RBC) exhibited any binding or phagocytosis.

TABLE 1

FcγRIIIA expression and Phagocytosis by COS-1 Cells Transfected with FcγRIIIA (γ and/or ζ).

| FcγRIIIA | MFI$^m$ | PI§ | Phagocytosis (% Cells +) | Rosetting (% Cells +) |
|---|---|---|---|---|
| α + pSVL (Sham) | 15 | 0 | 0 | 0 |
| α + γ | 254 | 129 ± 21.0 | 20 ± 5.0 | 48 ± 3.0 |
| α + ζ | 220 | 19 ± 3.2 | 3.8 ± 0.7 | 50 ± 1.7 |
| α + ζ + γ | 205 | 77 ± 5.0 | 16 ± 3.2 | 46 ± 2.0 |

Transfection efficiency was determined by flow cytometry. The mean fluorescence intensity (MFI) is shown for on or 3 separate experiments with similar results. Internalized RBCs were microscopically scored (1000×). Results are expressed as the mean ±SEM for phagocytosis and binding (rosetting) or EA. At least 3 separate experiments were performed for each clone. For each experiment, 1500 cells were counted at 5 randomly selected sites. * Mean Fluorescence Intensity. §PI (Phagocytic Index): number of RBCs internalized per 100 COS-1 cells Two Cytoplasmic Tyrosines of the γ Chain are Required for Phagocytosis:

To study the effect of the two conserved γ chain tyrosines on FcγRIIIA mediated phagocytosis, the N-proximal (clones M1A and M1B) or C-proximal (clones M2A and M2B) tyrosines were individually replaced by phenylalanine. For mutants with double tyrosine substitutions, both tyrosines were replaced by phenylalanine (DMA and DMB) (FIG. 1).

MFI measured by flow cytofluorimetry and % of positive cells with rosetting demonstrated similar surface expression of the receptor complexes in all transfectants bearing γ mutants and wild type γ (Table 2). These comparable levels of expression indicate that tyrosine residues in the cytoplasmic tail of the γ chain are not necessary for formation of the FcγRIIIA receptor complex required for surface expression. Results summarized in Table 2 are as follows: M1 γ mutants showed more than 99% reduction in phagocytic activity as shown by phagocytic index (PI) (<1% of transfectants with ingested EA and minimal ingested EA per phagocytosing cell) (p<0.02); M2 and DM γ mutants demonstrated essentially no phagocytosis (1 among 5000 cells examined) (Table 2, FIG. 2).

TABLE 2

FcγRIIIA expression and Phagocytosis by COS-1 Cells Transfected with FcγRIIIA -α/γ (wild type or mutants).

| FcγRIIIA | MR1$^m$ | PI§ | Phagocytosis (% Cells +) | Rosetting (% Cells +) |
|---|---|---|---|---|
| α + pSVL (Sham) | 15 | 0 | 0 | 0 |
| α + γ(WT) | 254 | 129 ± 21.0 | 20 ± 5.0 | 49 ± 3.0 |
| α + γ(M1A) | 259 | 0.3 ± 0.2 | 0.2 ± 0.1 | 49 ± 2.5 |
| α + γ(M1B) | 303 | 1.0 ± 1.0 | 1.0 ± 1.0 | 50 ± 1.5 |
| α + γ(M2A) | 232 | ≦0.04 | ≦0.02 | 49 ± 1.5 |
| α + γ(M2B) | 256 | ≦0.02 | ≦0.02 | 48 ± 3.0 |
| α + γ(DMA) | 222 | ≦0.02 | ≦0.02 | 48 ± 2.5 |
| α + γ(DMB) | 328 | ≦0.02 | ≦0.02 | 49 ± 2.0 |

See Table 1 for legend

Inhibition of Phagocytosis by Tyrophostin 23:

To investigate whether phagocytosis requires phosphorylation of tyrosine residues, COS-1 cells cotransfected with FcγRIIIA-α and wild type γ were incubated with increasing concentrations of tyrphostin 23 (tyr 23), an inhibitor of tyrosine kinases (Yaish et al, Science 242:933 (1988)). Tyr 23 decreased phagocytosis in a dose dependent manner, with 50% inhibition at 25 μM and complete inhibition at 200–400 AM (p<0.01) (Table 3) In contrast, tyr 23 did not affect the binding of EA. Inhibition of phagocytosis was not associated with reduction in viability, since transfectants pretreated with tyr 23 (400 μM) followed by washing had phagocytic activity partially (3 hr wash, Table 3) or completely (overnight wash, data not shown) restored.

TABLE 3

The Effect of Tyrphostin 23 (Tyr 23) on Phagocytosis by COS-1 Cells Transfected with FcγRIIIA-aly

| Tyr 23 (Concentration) | PI* | Rosetting (% Cells) |
|---|---|---|
| 0 μM | 125 ± 24 | 49 ± 3 |
| 25 μM | 68 ± 4 | 52 ± 9 |
| 50 μM | 26 ± 7 | 52 ± 8 |
| 100 μM | 16 ± 6 | 49 ± 7 |
| 200 μM | 1.2 ± 1 | 47 ± 5 |
| 400 μM | 0 | 48 ± 3 |
| 400 μM + washing | 63 ± 7 | 44 ± 6 |

*PI. Phagocytic Index

Tyrosine Residues of the γ Subunit are Phosphorylated In Vitro:

The possibility that tyrosine residues of the γ chain are phosphorylated was examined by in vitro kinase assays using COS-1 transfectants. Results shown in FIG. 4 demonstrate that the tyrosine residues of the wild type γ chains are phosphorylated in vitro. In contrast, the mutant γ chain transfectants and the shag transfectants showed no detectable phosphorylation. Since the single tyrosine substitution mutants (M1A and M2A) did not exhibit phosphorylation on the remaining tyrosine residues, it is likely that phosphorylation of either one of the two tyrosine residues requires the other tyrosine residue to be intact (FIG. 3). These phosphorylation data correlate well with the ability of the γ chain to induce a phagocytic signal, as substitution of either one of the tyrosine residues largely eliminates phagocytosis (Table 2, FIG. 2).

The in vitro kinase assay demonstrated a distinct band of approximately 40 kDa present in all lanes except the sham transfectants. This band may represent an associated phosphoprotein coprecipitating with γ.

Cytoplasmic Tyrosines of γ are Required for Mobilization of $Ca^{2+}$:

To examine whether the γ chain tyrosines are required for calcium mobilization, the calcium response following FcγRIIIA crosslinking was measured in individual transfected cells (WT, M1A, M2A or DMA) using digital video microscopy (FIG. 4). Epinephrine, which evokes a $Ca^{2+}$ signal in COS cells, was used as a positive control in all experiments. Transfectants with the WT receptor complex showed a typical transient calcium rise following crosslinking with biotinylated anti-FcγRIII followed by the addition of streptavidin or with anti-FcγRIII whole IgG. In 5 consecutive experiments (169 cells), 58% of cells responded to anti-FcγRIII with a calcium signal at least 50% as large as than induced by 10 μM epinephrine (FIG. 4, Table 4) In contrast, COS-1 cells transfected with either M1A, M2A or DMA showed markedly diminished calcium responses to anti-FcγRIII, although in cone of four experiments signifi cant calcium mobilization was evoked in M1A transfected COS-1 cells.

TABLE 4

The Effect of Tyrosiac Substitutions on Calcium Mobilization Evoked by Cross-Linking of FcγRIIIA

| FcγRIII | No. of Experiments | No. of Cells | % of Cells Responding* |
|---|---|---|---|
| α + γ (WT) | 5 | 169 | 57.8 |
| α + γ (M1A) | 4 | 123 | 16.0 |
| α + γ (M2A) | 4 | 117 | 2.8 |
| α + γ (DMA) | 4 | 70 | 3.7 |

*Cells were scored as responding if the calcium response was more than 50% of that observed with 10 μM epinephrine

EXAMPLE IV

Macrophage FcγRIII Signaling Induces Protein Tyrosine Kinase Activation

Specific tyrosine residues in the intracellular FcγRIIIγ subunit have been identified as necessary for signal transduction and subsequent effector functions, using NK cells and lymphocytes or fibroblasts transfected with chimeric or mutated receptors. (Darby et al, Blood 79:352A Nov. (1992)) FcγRIII in its native state on pulmonary macrophage or cultured monocytes (M) was examined in order to study the physiologically relevant protein tyrosine kinases (PTK) and phosphotyrosine containing substrates during macrophage signal transduction. Within seconds after FcγRIII crosslinking with Fab antibody, Western blot analysis revealed a characteristic pattern of phosphotyrosine substrates. This response was transient with most substrates peaking at 5 min. and declining after 10–20 min. Phosphotyrosine patterns were indistinguishable in fresh macrophage and cultured monocytes, validating the latter as a useful in vitro model. P62, a protein associated with p120$^{ras}$GAP, although not GAP itself, was identifier by specific immunoprecipitation as one of these phosphotyrosine substrates. A second substrate was found to be p95$^{vav}$, a hematopoietic oncogene product which is also tyrosine phosphorylated after TCR, sIg and FcεRI activation. The kinase PTK72/Syk, heretofore identified only in B cell sIg and mast cell FcεRI signaling, was also a major phosphotyrosine substrate after macrophage FcγRIII activation. In vitro kinase assays of anti-Syk immune complexes revealed a 3–4 fold increase in Syk autophosphorylation at 5–10 min. after receptor ligation. Syk has also been found to be present in immunoprecipitates of the γ chain FcγRIIIA suggesting that Syk is associated with phosphorylated γ chain.

EXAMPLE V

Antisense Oligonucleotides

Figure 5:
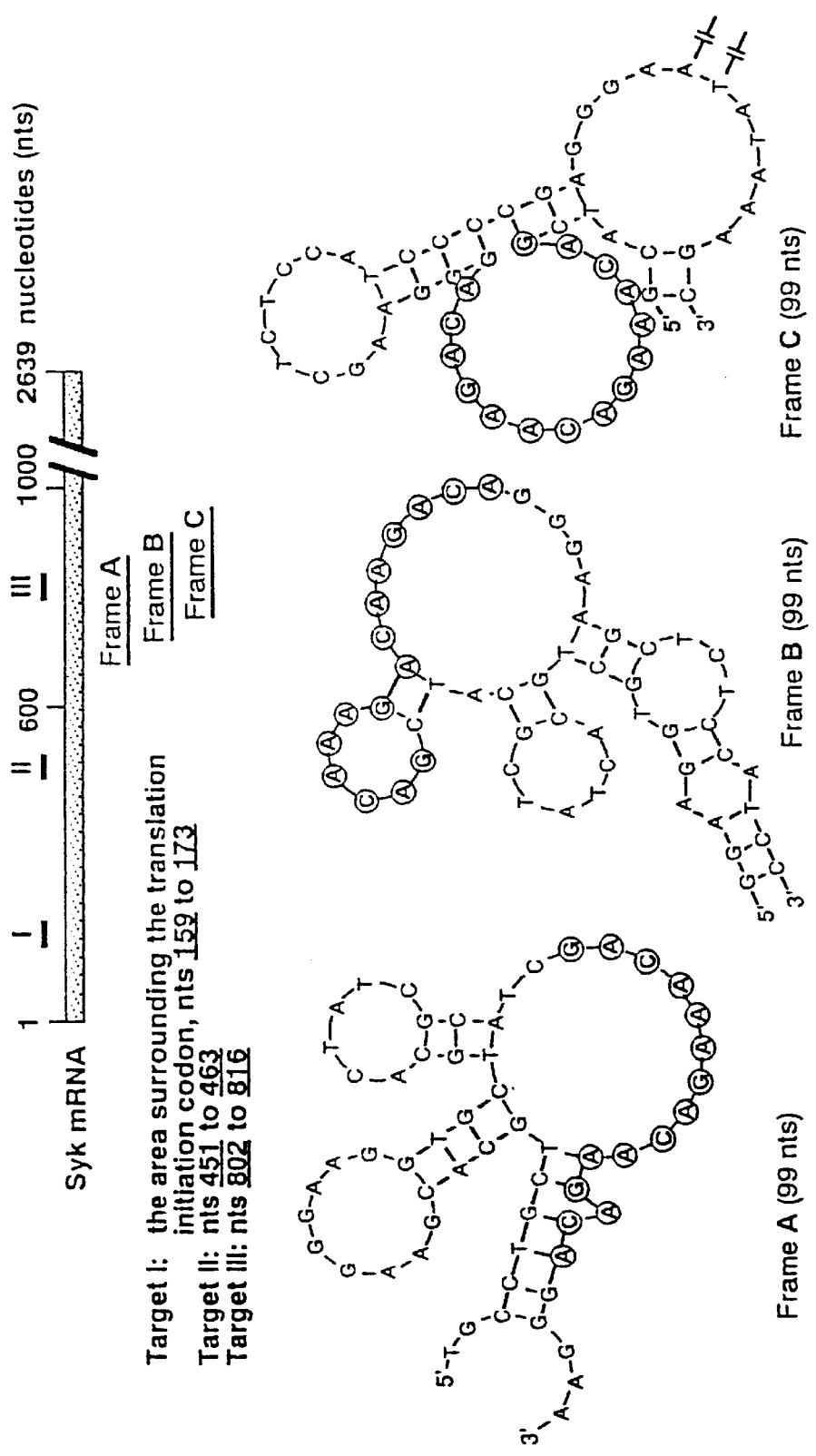
FIG. 5 shows selection of a target sequence (target III) for the stem-loop antisense ODN (SEQ ID NO:21 To SEQ ID NO:23). The entire Syk mRNA sequence was scanned three times with a RNA secondary structure prediction program to find sequences free of secondary structures. Each scanning was performed 33 bases apart in a 99-nucleotide frame (denoted as frames A, B, and C) sequentially. The most open sequence in three staggered scannings was chosen as a target sequence. The top rectangle with dots represents cDNA sequence of human Syk mRNA (Law et al, J. Biol. Chem. 269:12310 (1994)). The three target sites for the stem-loop Syk antisense ODN are shown above the Syk mRNA sequence line as three short solid lines, denoted I, II, and III. Target sites I, II and III correspond to nucleotides no. 159 to 173 (the area surrounding the translation initiation codon), no. 451 to 463 and no. 802 to 816, respectively. Target III is shown as an example in this Figure. Targets I and II were chosen in the same manner. Putative secondary structures in the area of Syk mRNA containing the target III sequence are shown in the three staggered frames of 99 nts each, frame A, frame B, and frame C. Circled nucleotides in the three staggered frames are the common sequence of target III with minimum secondary structures.
Figure 6:
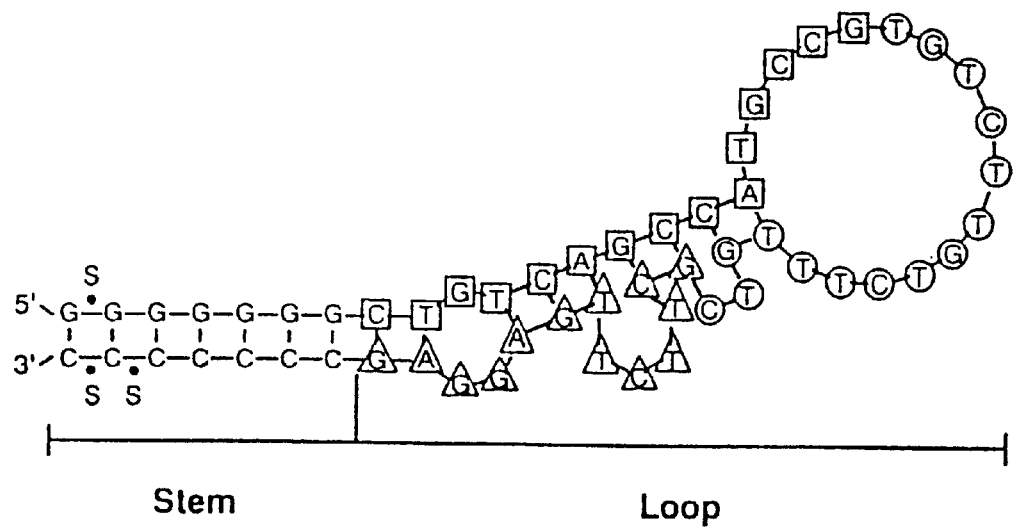
FIG. 6 shows secondary structure of the stem-loop Syk antisense ODN (SEQ ID NO:24). The stem domain of the nucleotide length is formed by complementary terminal sequence with nucleotide content of only G and C in the 5' and 3' termini. The loop domain consists of three antisense sequences; the 5'-CTGTCAGCCATGCCG-3' (SEQ ID NO:29) sequence shown with squares is complementary to target I in Syk mRNA (see FIG. 5), the 5'-GCTTCTTGAGGAG-3' (SEQ ID NO:30) sequence shown in triangles is complementary to target II, and the 5'-TGTCTTGTCTTTGTC-3' (SEQ ID NO:31) sequence shown with circles is complementary to target III which is also denoted with circles in FIG. 5. The three different antisense sequences were tandemly joined in the 5' to 3' order for targets I, III, and II, respectively. MS indicates the phosphorothioate modification, the 5-prime terminus has one phosphorothioate modification and the 3-prime terminus has two.

Two antisense oligonuclectides (ODN) were designed for human Syk mRNA. A linear antisense ODN was used to target the area surrounding the translation initiation codon. The other was designed to have a stem-loop structure, which can hybridize to three different sites of human Syk mRNA. These Syk antisense ODNs were employed to investigate the role of the Syk tyrosine kinase in the Fcγ receptor mediated phagocytic signal in cultured monocytes. Construction of antisense oligodeoxynucleotides: Antisense or scrambled control ODNs were modified to be protected from nucleases. One phosphodiester backbone at the 5-prime terminus and two at the 3-prime terminus were modified with phosphorothioate. Prediction of secondary structures of Syk mRNA (Law et al, a. Biol. Chem. 269:12310 (1994)) and ODNs were carried out with the MacDNASIS program (Hitachi Software, San Bruno, CA) on a Macintosh computer. Linear 17 mer Syk antisense ODN, having the sequence of 5'-CGCTGTCAGCCATGCCG-3' (SEQ ID NO:9), targets the area surrounding the translation initiation codon of Syk mRNA. Stem-loop Syk antisense ODN is a 57 mer containing sequences complementary to three different target sites, target I (the area of the translation initiation, nucleotide no. 159 to 173), target II (451 to 463), and target III (802 to 816) of Syk mRNA (Law et al, J. Biol. Chem. 269:12310 (1994)) (FIG. 5). The stem-loop Syk antisense ODN forms a stem and loop structure by itself and was designed to contain minimal intramolecular secondary structures in the loop domain (FIG. 6). The sequence of the stem-loop Syk antisense ODN is 5'-GGGGGGGCTGTCAGCCATGCC GTGTCTTGTCTTTGTCGCTTCTTGAGGAGCCCCCC C-3' (SEQ ID NO:10). Linear 17 mer control ODN has a random sequence of 5'-GCCCAAGATGATTCCAG-3' (SEQ ID NO:11). Stem-loop 61 mer control ODN has a random sequence of 5'-ATGGAATCATCTTGCGCA TTCATTCGTTCCTCAAAGAAGAATATGAA-3' (SEQ ID NO:12) within the loop domain. The linear and stem-loop control ODNs were also modified at both the 5-prime and 3-prime termini by phosphorothioates.

Preparation of liposomes: One μg each of the control scrambled phosphodiester ODNs, the linear and stem-loop Syk antisense ODNs in 50 μl of PBS were incubated with 4 μg (2 μl) of LIPOFECTAMINE™ (GIBCO BRL, Life Technologies, Inc. Gaithersburg, Md.). The ODN-liposome complexes were allowed to form at the room temperature for 45 min.

Monocytes isolation and culture: Peripheral blood mononuclear cells from healthy individuals were isolated by a standard adherence procedure (Darby et al, J. Immunol. 152:5429 (1994)). Briefly, the heparinized blood was centrifuged on Ficoll-Hypaque (Lymphocyte Separation Medium; Organon Teknika, Durham, N.C.) and interface cells were washed twice in PBS. Mononuclear cells were resuspended in complete medium containing RPMI 1640 (GIBCO BRL, Life Technologies, Inc. Gaithersburg, Md.) with 10% heat-inactivated FCS and 2 mM L-glutamine. Cells were allowed to adhere at 37° C. onto tissue culture flasks precoated with FCS. After 45 to 90 min non-adherent cells were removed with extensive washing in HBSS. Cells were harvested by vigorous agitation. The yield of monocytes ranged from 2–6×10$^7$ cells/500 ml of blood. Monocytes were routinely more than 98% viable judged by trypan blue exclusion. Isolated monocytes were maintained in RPMI 1640 supplemented with L-glutamine (2 mM) and 10% heat-inactivated FCS at 37° C. with 5% CO$_2$.

Oligodeoxynucleotides treatment of cells. 1×10$^5$ Monocytes were incubated with ODN-liposome complexes containing 2 μg/ml of LIPOFECTAMINE and 0.5 μM of the linear control, 0.5 μM of the linear Syk antisense ODN or 0.1 μM of the stem-loop control, 0.1 μM of the stem-loop Syk antisense ODN in 0.3 ml of RPMI 1640 medium without FCS in a 24-well plate (Falcon; Becton Dickinson Labware, Lincoln Park, N.J.) at 37° C. for 4 h. Medium was added to a 1 ml final volume with RPMI 1640 containing 10% FCS and cells were then incubated at 37° C. for 2 days. The same volume of ODN-liposome mixture was also added to each well on Day 2, indicating that 1×10$^5$ monocytes were incubated with ODN-liposome complexes containing 4 μg/ml of LIPOFECTAMINE and 1.0 μM of the linear control, 1.0 μM of the linear Syk antisense ODN or 0.2 μM of the stem-loop control, or 0.2 µM of the stem-loop Syk antisense ODN for 2 days.

Preparation of IgG-sensitized red blood cells (EA): $1\times10^9$ Sheep red blood cells (RBCs)/ml (Rockland Inc., Gilbertville, Pa.) were sensitized with an equal volume of the highest subagglutinating concentration of rabbit anti-sheep RBC antibody (Cappel Laboratories, West Chester, Pa,) at 37° C. for 30 min. The IgG-sensitize& RBCs were washed twice and resuspended in PBS to a final concentration of $1\times10^9$ RBCs/ml as described previously (Schreiber et al, J. Clin. Invest. 56:1189 (1975)).

Phagocytosis of IgG-sensitized RBCs (EA): Monocytes treated with antisense ODNs were incubated at 37° C. for 30 min with EA at a ratio of 100:1 (EA to monocytes). Cells were briefly exposed to hypotonic PBS to remove adherent EA. The cells were then stained with Wright-Giemsa and phagocytosed RBCs were microscopically scored ($\times 1000$). One hundred monocytes were chosen in a random manner and then internalized EA were expressed as the phagocytic index.

Flow cytometry analysis: Monocytes were incubated with anti-FcγRI (32.2) (Indik et al, Blood 83:2072 (1994)) or anti-FcγRII (IV.3) (Indik et al, Blood 83:2072 (1994)) or anti-FcγRIII (3G8) moAb (Park et al, J. Clin. Invest. 92:1967 (1993), Park et al, J. Clin. Invest. 92:2073 (1993)) at 4° C. for 30 min, then washed twice with calcium and magnesium-free PBS containing 0.1 bovine serum albumin (BSA) and 0.02% sodium azide and labeled with FITC-conjugated goat anti-mouse F(ab')2 IgG (Tago, Burlingame, Calif.) at 4° C. for 30 min. Cells were then washed and fixed with 1% paraformaldehyde. Fluorescence was measured on a FACStar (Becton Dickinson, Mountain View, Calif.), and mean fluorescence intensity data and contour plots were generated using Consort 30 software. For all samples, 10,000 events were recorded or a logarithmic fluorescence scale.

Reverse transcribed polymerase chain reaction (RT-PCR): Total RNA was isolated from monocytes treated with scrabbled control and Syk antisense ODNs. cDNA-was synthesized from total RNA with random hexanucleotide primers (Boehringer Mannheim, Indianapolis, Ind.). PCR was performed with synthesized cDNA as templates with two primers. Syk-H primer: 5'-GGTGTGTGCCCT CCGGCC-3' (SEQ ID NO:13) corresponding to nucleotide No. 122 to 139 of Syk mRNA (Law et al, J. Biol. Chem. 269:12310 (1994)), Syk-M primer: 5'-CTGCAGGTT CCATGT-3' (SEQ ID NO:14) (nucleotide No. 550 to 564). The PCR products were analyzed by Southern hybridization.

Southern hybridization. RT-PCR products were electrophoresed on a 1.5% agarose gel. DNA was transferred onto a nylon membrane (NEN Research Products, Boston, Mass.). The transferred membrane was hybridized with biotinylated internal probe (Syk-pS: 5'-GGGAGT GGTAGTGGCAGAGC-3' (SEQ ID NO:15), nucleotide No. 408 to 427) in 6×SSPE and 50% formamide. After washing the membrane in 0.1×SSC at 50° C., the hybridized bands were visualized by chemiluminescent detection reagent (PROTOGENE™ Nucleic Acid Detection System, GIBCO BRL, Life Technologies, Inc. Gaithersburg, Md.).

Results

Figure 7:
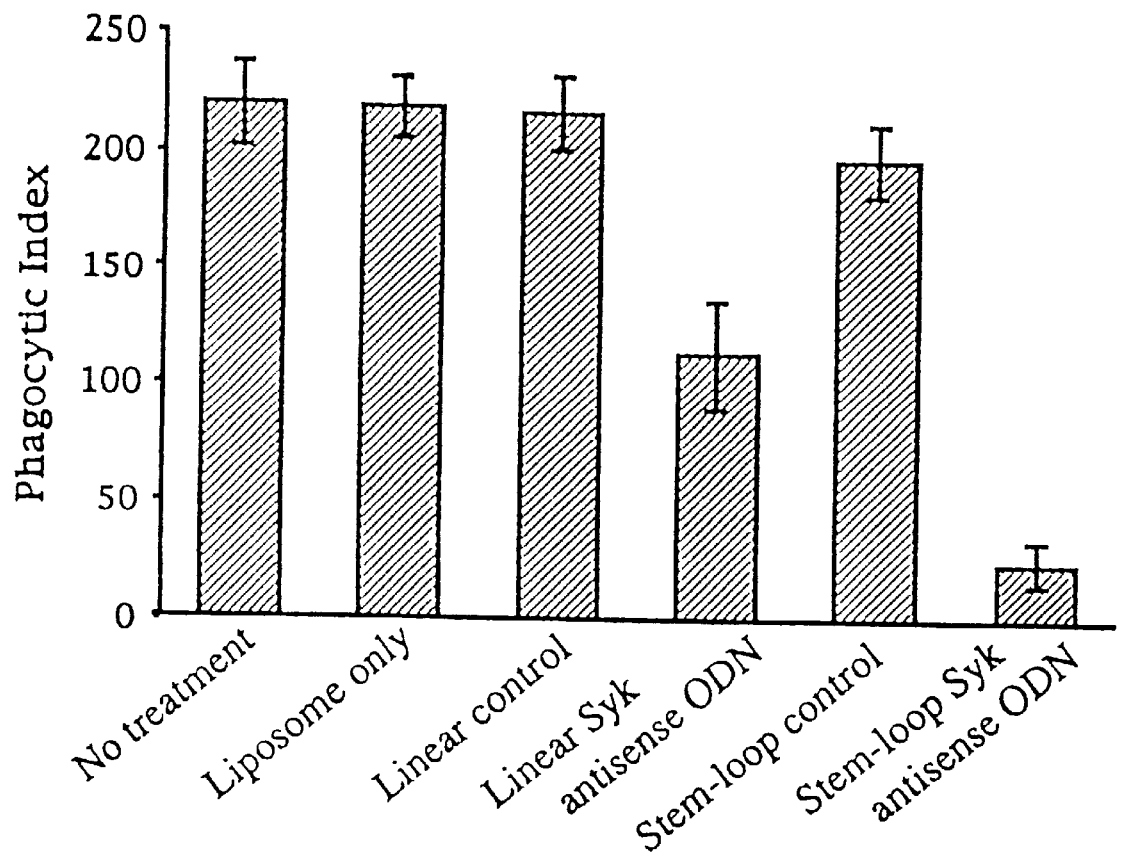
FIG. 7 shows inhibition of Syk antisense ODNs on phagocytosis in monocytes. Monocytes ($1 \times 10^5$ cells/ml) were incubated with complexes of 4 μg/ml of LIPO-FECTAMINE and ODNs (1.0 μM each of the linear control or the linear Syk antisense ODNs, or 0.2 μM each of the stem-loop control or the stem-loop Syk antisense ODN) for 2 days, and the phagocytosis of IgG-sensitized red blood cells (EA) was examined. Phagocytic index (PI)=number of ingested RBCs/100 cells. Each bar represents the mean ±SEM of three separate experiments.

Monocytes incubated with the linear Syk antisense ODN (1 µM) exhibited a reduced level of phagocytosis. Phagocytosis reduced by 49%, shown as the phagocytic index (PI, from 220±8.8 to 113±12.3). Monocytes incubated with the stem-loop Syk antisense ODN (0.2 µM) exhibited an even greater reduction in phagocytosis by 89% (PI from 220±8.8 to 24±4.2) (FIG. 7). Both scrambled control ODNs, the linaer (1 µM) or stem-loop (0.2 µM) ODN, did not significantly affect FcγRIIA mediated phagocytosis. Similarly, liposomes alone did not reduce FcγRIIA mediated phagocytosis. FcγRII expression did not change with any of the treatments as measured by flow cytometric analysis in cultured monocytes. These results demonstrate that the Syk tyrosine kinase is a major signal transducer for the FcγRIIA mediated phagocytosis in monocytes and indicate that association between FcγRIIA and the Syk kinase (as well as tyrosine phosphorylation) are important in phagocytosis of IgG-coated cells.

Figure 8:
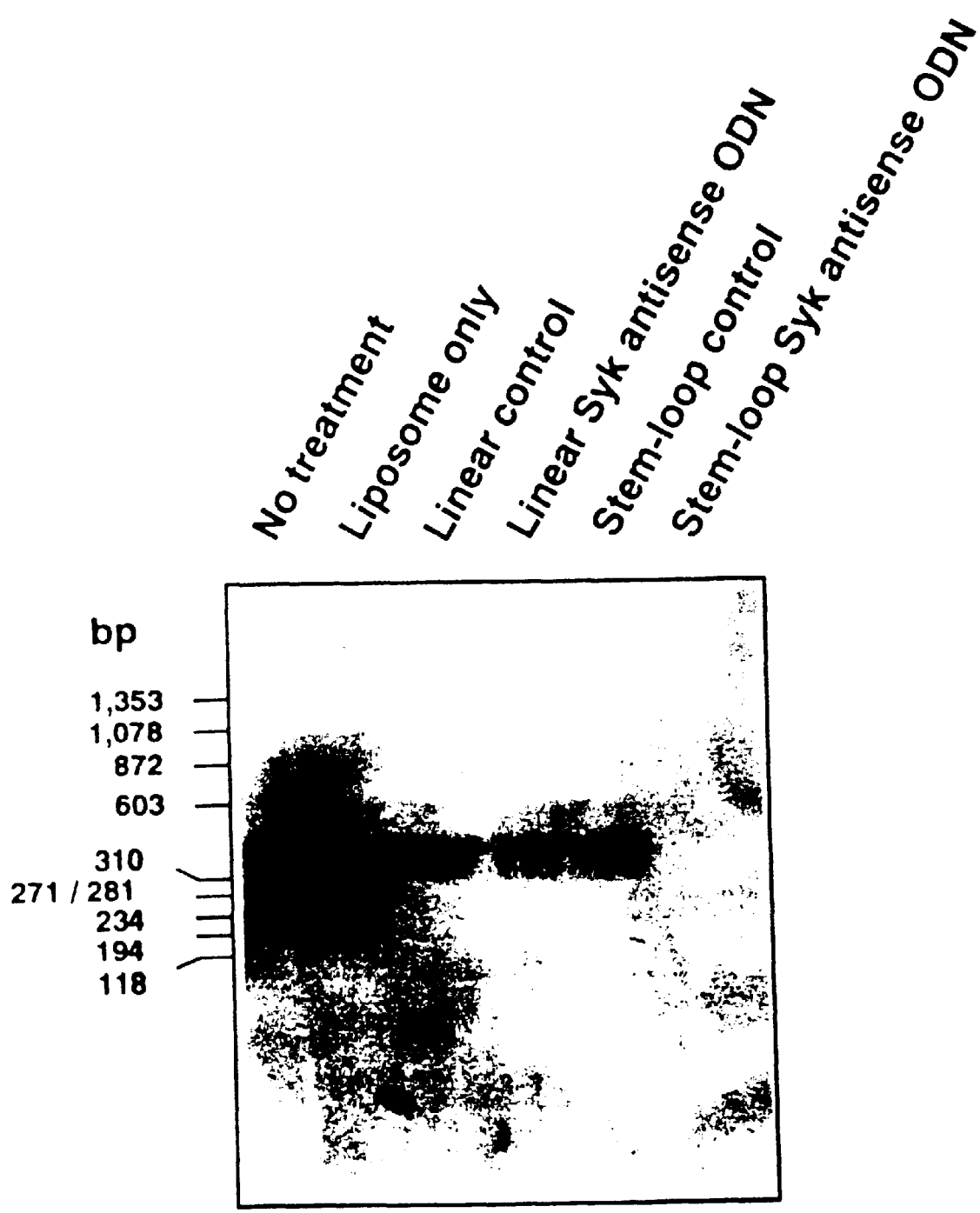
FIG. 8. Effect of Syk antisense ODNs on Syk mRNA in monocytes. Total RNA was isolated from monocytes ($1 \times 10^5$ cells/ml) treated with complexes of 4 μg/ml of LIPO-FECTAMINE and the ODNs (1.0 μM each of the linear control or the linear Syk antisense ODN, or 0.2 μM each of the stem-loop control or the stem-loop Syk antisense ODN) for 2 days, and cDNA was synthesized from total RNA with random hexanucleotide primers. PCR was performed with Syk cDNA as templates with two Syk primers (Syk-H and Syk-M). PCR products were analyzed by Southern hybridization and hybridized bands were visualized by chemiluminescent detection reagents.

Next, it was determined whether the reduced phagocytosis in monocytes correlated with Syk mRNA levels. Quantitative RT-PCR (reverse transcribed-polymerase chain reaction) was employed to determine intracellular levels of Syk mRNA in monocytes. Total RNA was isolated from monocytes ($1\times10^5$ cells/ml) treated with Syk antisense ODNs and used to synthesize the first strand cDNA. As shown in FIG. 8, the linear Syk antisense ODN (1.0 µM) substantially reduced Syk mama. The stem-loop Syk antisense ODN (0.2 µM) completely eliminated Syk mRNA (FIG. 8). In contrast, two scrambled control ODNs (1.0 µM of the linear control or 0.2 µM of the stem-loop control) as well as liposomes alone did not reduce Syk mRNA. These results show that Syk antisense ODNs, both the linear and stem-loop ODNs, are able to degrade Syk mRNA in a sequence specific manner in monocytes. Furthermore, the stem-loop Syk antisense ODN showed its efficacy over linear antisense molecules for targeting mRNA.

EXAMPLE VI

Inhibition of Histamine Release by Stem-loop Syk Antisense Oligonucleotides (ODNs)

Experimental design

Cell culture: RBL-2H3 cells (histamine containing rat mast cells) were grown in minimal essential medium supplemented with 17% fetal bovine serum, 100 U of penicillin and 100 µg of streptomycin per ml and 4 mM glutamine at 37° C. in 5% $CO_2$. Cells were seeded onto 1.6 cm plates or 24 well planes at a concentration of $1\times10^5$ cells per well for 24 h before assay.

Figure 9:
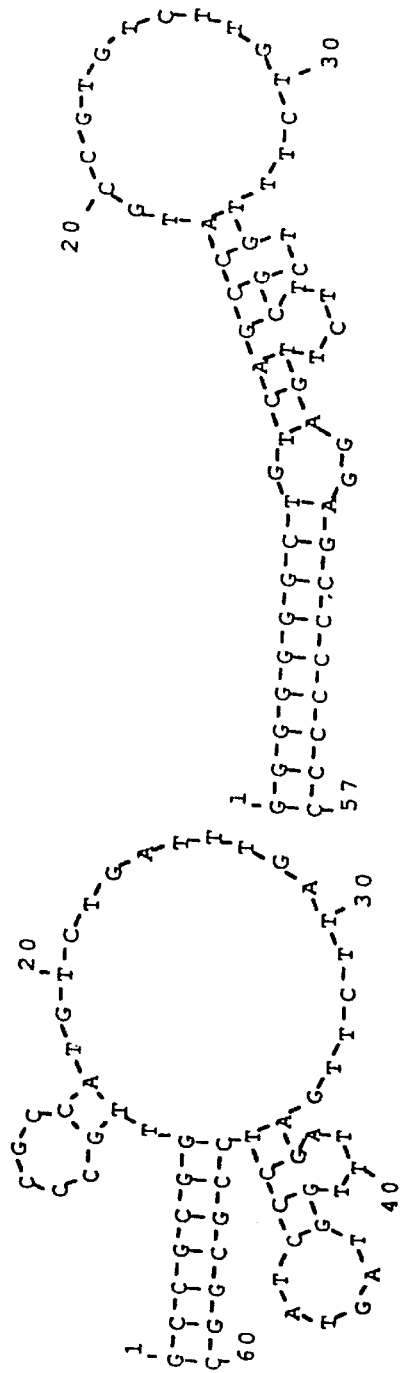
FIG. 9. Comparison of rat and human Syk antisense (SEQ ID NOs:25–28).

Construction of antisense ODNs: To protect from nuclease digestion, antisense and sense control ODNs were modified by adding one phosphorothioate at the 5-prime terminus and two at the 3-prime terminus of the phosphodiester backbone. Three linear Syk antisense ODNs were designed: Target-I linear Syk antisense ODN (5'ATTGCCCGCCATGTCT3' (SEQ ID NO:16), nucleotides 319 to 333 including the translating initiation codon of Syk mRNA), Target-II (5'GATTTGATTCTTGAG3' (SEQ ID NO:17), nucleotides 1175 to 1189), Target-III (5'ATTTGGTAGTATCCCT3' (SEQ ID NO:18), nucleotides 1465 to 1479). Stem-loop Syk antisense ODN is a 60 mer comprising sequences complementary to the three target sites (FIG. 9) (see also Example V above).

ODN treatment of cells: $5\times10^4$ or $1\times10^5$ RBL-2H3 cells were seeded in each well of a 24 well plate 24 hr before lipofection details. ODN-liposome complexes were added twice, once on day 2 and once on day 3. Each time, 4 µl DOTAP (a "lipofectamine") (1 µg/1 µl stock) and 2 µl ODN (1 µg/µl) were allowed to form complexes in EMEM (75 µl total volume). The ODN-liposome complexes were added to each well containing 175 µl culture medium without serum. The cells were incubated at 37° C. for 24 hr. A second volume of ODN-liposome complexes (75 µl) was added, the culture medium was adjusted to 5% FCS (final volume 1.0 ml) and the transfected RBL-2H3 cells were incubated a 37° C. for one additional day before assay for histamine release.

Reverse transcribed polymerase chain reaction (RT-PCR): Total RNA was isolated from RBL-2H3 cells treated with Syk sense control or Syk antisense ODN. cDNA was synthesized from total RNA with random hexanucleotide primers and oligo (d)T, PCR was performed with synthesized cDNA as templates using two primers, Rat-5 Syk: 5'-TTTGGCAACATCACCCGG-3' (SEQ ID NO:19) (nucleotides 368 to 386 and Rat-3 Syk primer; 5'-ACTTATGATGGCTTGCTC-3' (SEQ ID NO:20) (nucleotides 748 to 762). γ chain and β-actin primers were used as a control.

Histamine release assay: The histamine release assay was performed by cross-linking the rat RBL-2H3 cell IgE receptor FcεRI as described below, and measuring histamine release using an enzyme immunoassay kit (Immunotech, France). Twenty four well plates containing $1 \times 10^5$ RBL-2H3 cells per well in 1.0 ml EMEM were incubated overnight at 37° C. The cells were washed once with PBS and incubated on ice with 1.0 ml PAGCM (a standard histamine release buffer) and 100 µl of FcεRI antibody for 30 min. Following one gentle wash with PBS, the RBL-2H3 cells were incubated as follows: 1.0 ml of PAGCM buffer alone (negative control), 1.0 ml of PAGCM buffer containing 10 µl of calcium ionophore (50 µg/ml stock) (positive control), or 1.0 ml of PAGCM containing 10 µM of coat anti-mouse antibody (1 mg/ml) for 30 min. at 37° C. The PAGCM buffer containing histamine was removed from the cells and assayed by enzyme immunoassay. One hundred µl standards were included to produce a standard curve.

Results

Figure 10:
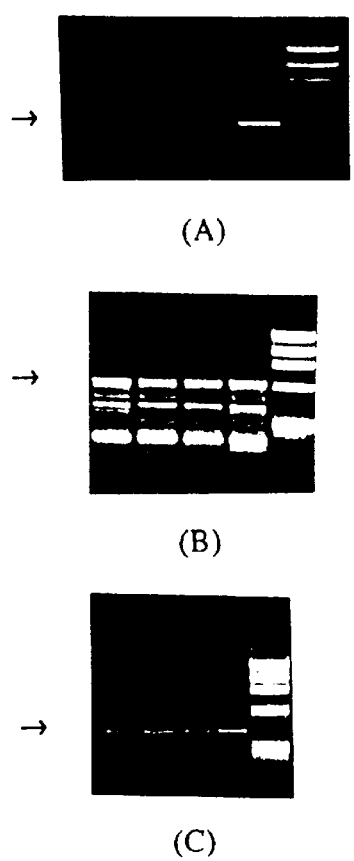
FIG. 10. Inhibition of Syk kinase expression in RBL-2H3 cells by stem-loop rat Syk antisense oligonucleotides (ODN). A. Examination of Syk expression by RT-PCR using rat Syk primers. Lane 1, cells treated with Syk antisense ODN: Lane 2, cells treated Syk sense ODN; lane 3, reagent control; Lane 4, no treatment; Lane 5, molecular weight markers. B. Examination of β-actin expression by RT-PCR using rat β-actin primers. Lane 1, cells treated with Syk antisense ODN; Lane 2, cells treated with Syk sense ODN; Lane 3, reagent control; Lane 4, no treatment; Lane 5, molecular weight markers. -=β-actin. C. Examination of FcεRI γ chain expression by RT-PCR using γ chain primers in rat Syk anisense ODN treated RBL-2H3 cells. Lane 1, cells created with Syk antisense ODN; Lane 2, cells treated with Syk sense ODN; Lane 3, reagent control; Lane 4, no treatment; Lane 5, molecular weight markers. -=γ chain.

The data presented in FIG. 10A demonstrate that Syk expression in RBL-2H3 cells is markedly inhibited by the presence of Syk antisense ODN but not by the presence of Syk sense ODN. Treatment of R3L-2H3 cells with Syk antisense ODN does not affect β-actin expression (FIG. 10B). Similarly, treatment of RBL-2H3 cells with Syk antisense ODN does not affect γ chain expression.

Following FcεRI and goat anti-mouse antibody crosslinking, RBL-2H3 cells treated with stem-loop Syk antisense ODNs released 74% less histamine compared to control cells treated with sense DNA.

|  | Anti-FcεRI and Goat antimouse antibody |
|---|---|
| Sense DNA | 1.9 ng of histamine released |
| Antisense | 0.5 ng of histamine released (740% inhib.) |

All documents cited above are incorporated herein by reference.

While the invention has been describe, in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of inhibiting the phagocytic potential of a cell comprising introducing into said cell FcγRIIB in an amount such that said inhibition is effected.

2. The method according to claim 1 wherein said cell is a macrophage.

3. The method according to claim 1 wherein said cell expresses FCγRIIA.

4. The method according to claim 1 wherein a construct comprising a sequence encoding FcγRIIB is introduced into said cell.

* * * * *